（12) United States Patent
Oukhatar et al.

(10) Patent No.: US 12,269,837 B2
(45) Date of Patent: Apr. 8, 2025

(54) BIFUNCTIONAL do2pa DERIVATIVES, CHELATES WITH METALLIC CATIONS AND USE THEREOF

(71) Applicants: CENTRE NATIONAL DE LA RECHERCHE SCIENTIFIQUE (CNRS), Paris (FR); UNIVERSITE DE BRETAGNE OCCIDENTALE, Brest (FR)

(72) Inventors: Fatima Oukhatar, Brest (FR); Maryline Beyler, Brest (FR); Raphaël Tripier, Kersaint-Plabennec (FR)

(73) Assignees: CENTRE NATIONAL DE LA RECHERCHE SCIENTIFIQUE (CNRS), Paris (FR); UNIVERSITÉ DE BRETAGNE OCCIDENTALE, Brest (FR)

( * ) Notice: Subject to any disclaimer, the term of this patent is extended or adjusted under 35 U.S.C. 154(b) by 308 days.

(21) Appl. No.: 17/648,688

(22) Filed: Jan. 24, 2022

(65) Prior Publication Data
US 2022/0143230 A1 May 12, 2022

Related U.S. Application Data

(62) Division of application No. 16/579,133, filed on Sep. 23, 2019, now Pat. No. 11,266,754, which is a division of application No. 15/533,204, filed as application No. PCT/EP2015/078732 on Dec. 4, 2015, now abandoned.

(30) Foreign Application Priority Data

Dec. 5, 2014 (EP) .................................... 14196637

(51) Int. Cl.
| | | |
|---|---|---|
| C07D 401/12 | (2006.01) |
| A61K 51/10 | (2006.01) |
| C07D 213/79 | (2006.01) |
| C07D 257/02 | (2006.01) |
| C07D 401/06 | (2006.01) |
| C07F 7/24 | (2006.01) |
| C07F 9/6524 | (2006.01) |
| C07F 9/94 | (2006.01) |

(52) U.S. Cl.
CPC ............ C07F 9/94 (2013.01); A61K 51/1093 (2013.01); C07D 213/79 (2013.01); C07D 257/02 (2013.01); C07D 401/06 (2013.01); C07D 401/12 (2013.01); C07F 7/24 (2013.01); C07F 9/6524 (2013.01); A61K 2123/00 (2013.01)

(58) Field of Classification Search
CPC .................................................. C07D 401/12
See application file for complete search history.

(56) References Cited

U.S. PATENT DOCUMENTS

| | | |
|---|---|---|
| 5,006,643 A | 4/1991 | Fazio et al. |
| 5,641,870 A | 6/1997 | Rinderknecht et al. |
| 5,756,065 A | 5/1998 | Wilson et al. |
| 2016/0115187 A1 | 4/2016 | Tripier et al. |

FOREIGN PATENT DOCUMENTS

| | | |
|---|---|---|
| EP | 0296522 A2 | 12/1988 |
| WO | 2014195416 A1 | 12/2014 |

OTHER PUBLICATIONS

Lima et al., "H2Me-do2pa: An Attractive Chelator with Fast, Stable and Inert natBi3+ and 213Bi3+ Complexation for Potential α-radioimmunotherapy Applications," Chemical Communications, vol. 50, 2014, pp. 12371-12374.

Rodriguez-Rodriguez et al., "Lanthanide(III) Complexes with Ligands Derived from a Cyclen Framework Containing Pyridinecarboxylate Pendants. The Effects of Steric Hindrance on the Hydration Number," Inorganic Chemistry, vol. 51, No. 4, 2012, pp. 2509-2521.

(Continued)

Primary Examiner — Brian E McDowell
(74) Attorney, Agent, or Firm — NIXON & VANDERHYE

(57) ABSTRACT

Disclosed are chelates resulting from the complexation of bifunctional do2pa derivatives ligands of formula (I), wherein the substituents $R^1$, $R^{1'}$, $R^2$, $R^{2'}$, $R^3$, $R^{3'}$, $L^1$, $L^{1'}$, $L^2$ and $L^{2'}$ are defined as in the claims, with metallic cations, especially Pb(II) and Bi(III). Also disclosed are bifunctional do2pa derivatives ligands of formula (I), as well as the use of chelates in nuclear medicine and the use of ligands in cations detection or epuration of effluents.

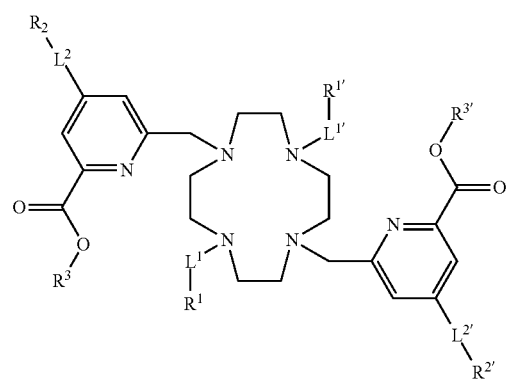

15 Claims, No Drawings

(56) References Cited

OTHER PUBLICATIONS

Halime et al., "Coordination of Bismuth and Lead in Porphyrins: Towards an in-situ Generator for α-radiotherapy?," Biochimie, vol. 91, 2009, pp. 1318-1320.
Mato-Iglesias, et al., "Lanthanide Complexes Based on a 1,7-Diaza-12-crown-4 Platform Containing Picolinate Pendants: A New Structural Entry for the Design of Magnetic Resonance Imaging Contrast Agents," Inorganic Chemistry, vol. 47, 2008, pp. 7840-7851.
International Search Report issued in Application No. PCT/EP2015/078732, dated Feb. 2, 2016.

BIFUNCTIONAL do2pa DERIVATIVES, CHELATES WITH METALLIC CATIONS AND USE THEREOF

CROSS-REFERENCE TO RELATED APPLICATIONS

This application is a divisional of U.S. Ser. No. 16/579,133 filed Sep. 23, 2019, which is a divisional of U.S. Ser. No. 15/533,204 filed Jun. 5, 2017, which was a national stage application, filed under 35 U.S.C. § 371, of International Patent Application No. PCT/EP2015/078732 filed Dec. 4, 2015, which claims priority to EP application No. 14196637.4 filed Dec. 5, 2014. Each of the previously noted applications is hereby incorporated by reference herein in their entirety.

FIELD OF INVENTION

The present invention relates to chelates resulting from the complexation of bifunctional do2pa derivatives with metallic cations, especially Pb (II) and Bi (III). The invention further relates to bifunctional do2pa derivatives ligands. Another object of the invention is the use of chelates of the invention in nuclear medicine and the use of ligands of the invention in cations detection or epuration of effluents.

BACKGROUND OF INVENTION

Tetraazamacrocycles such as derivatives of cyclen (1,4,7,10-tetraazacyclododecane) generate an important interest in many fields such as medicine, especially nuclear medicine; epuration of effluents contaminated with radioactive elements or metals such as lead; catalysis; solid/liquid extraction and liquid/liquid extraction; or detection of traces of metallic cations. The present invention relates to all these fields of applications, especially nuclear medicine.

In nuclear medicine, radiopharmaceuticals used as therapeutic agents or as imaging agents often comprise chelates of radioelements. Depending on the nature of the radionuclide, it is for example possible to perform PET imaging (Positron Emission Tomography), SPECT (Single Photon Emission Computed Tomography) or RIT (RadioImmuno-Therapy).

RIT involves an antibody labeled with a radionuclide to deliver cytotoxic radiation to a target cell, especially tumor cells. In RIT, alpha emitters are preferred since alpha radiation has a short path length in human tissues. The energy of the alpha radiation is therefore absorbed in a smallest zone, enabling a better destruction of target cells with few damages to adjacent healthy tissues. Alpha emitters being studied for RIT are especially $^{212}$Bi and $^{213}$Bi.

However, the use of $^{212}$Bi and $^{213}$Bi faces several difficulties.

First of all, these radionuclides should be used under the form of chelates in reason of their high toxicity under free ionic form. Bismuth chelates are usually prepared using tetraazacycloalcanes ligands.

Secondly, bismuth oxides quickly precipitate in aqueous media at pH higher than 2. It is therefore necessary to chelate them in acidic medium.

Another difficulty is that half-lives of $^{212}$Bi (60.6 min) or $^{213}$Bi (45.6 min) are too short to enable preparation of the chelates and their administration while retaining sufficient time for biodistribution and action on target cells. In order to overcome this difficulty, an in situ generator of $^{212}$Bi is thus often used, involving the isotopic parent of $^{212}$Bi, $^{212}$Pb, which has a longer half-life (11 hours).

When an in situ $^{212}$Pb/$^{212}$Bi generator is used, a ligand able to chelate $^{212}$Pb should be used to form the chelate. Then, $^{212}$Pb converts spontaneously into $^{212}$Bi within the chelate. The ligand should thus be able to chelate as stably both Bi(III) and Pb(II) in order to avoid release of free bismuth after conversion from lead. Even if half-life of $^{212}$Pb is longer than the one of $^{212}$Bi, complexation kinetics need to be fast to provide high specific activities.

While there are many ligands capable of chelating lead, there is only a few ligands capable of stably chelating bismuth, and even less capable of stably chelating both bismuth and lead.

Among polyazamacrocyclic ligands which were evidenced to have a good affinity for bismuth or lead, tetraazacycloalcanes and porphyrines present the best affinities for these metals.

However, only one porphyrinic ligand was shown to have affinity for both bismuth and lead (Halime et al., Biochimie, 2009, 91, 1318-1320). Moreover, the synthesis of this kind of ligand is long and difficult and resulting chelates are quite insoluble in water.

Tetraazacycloalcanes are simpler to synthesize and are widely used for numerous applications. However, even if compounds such as dotam are interesting for chelation of lead, none of these types of ligands has a real affinity for bismuth, especially for nuclear medicine applications. Indeed they have slow complexation kinetics compared to the half-life of the radionuclide and/or they are instable in vivo.

The Applicant developed a tetraazamacrocycle based on 1,4,7,10-tetraazacyclododecane and picolinate coordinating groups, H$_2$Me-do2pa (Rodriguez-Rodriguez et al., Inorg. Chem., 2012, 51, 2509-2521) The Applicant recently evidenced that H$_2$Me-do2pa was suitable to stably chelate Bi(III) (Lima et al., Chem. Commun., 2014, 50, 12371-12374). The complexation properties of H$_2$Me-do2pa towards Bi(III) revealed fast formation of the chelate, even in acidic medium. Resulting chelate has a high thermodynamic stability and is stable in vitro. Radiolabelling was performed using directly $^{213}$Bi. However, in situ $^{212}$Pb/$^{212}$Bi generator was not assessed and affinity for Pb-212 was not investigated.

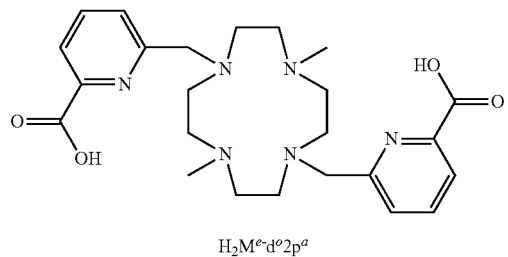

H$_2$M$^e$-d$^o$2p$^a$

The Applicant further studied H$_2$Me-do2pa ligand and recently evidenced that it is suitable to stably chelate both Bi(III) and Pb(II) (not yet published—PCT/EP2014/061723). Metallation kinetics are fast for both bismuth and lead. Thermodynamic stability and kinetic inertness are also good for both bismuth and lead. Moreover, the Bi and Pb chelates are well soluble in water. Therefore, H$_2$Me-do2pa ligand presents suitable properties to be used with an in situ $^{212}$Pb/$^{212}$Bi generator and meets specifications required for optimized chelates intended to be used in nuclear medicine.

However, to be valuable for various applications, and especially for biological applications, such ligands need to be functionalizable. Especially, for applications in nuclear medicine, the chelate need to be bioconjugated to a targeting biomolecule while trapping the radionuclide, leading to a bifunctional chelating agent (BCA). Obtaining a BCA requires the introduction of an appropriate coupling function in the structure of the metal chelator, to allow for the bioconjugation prior or after labeling with the radioisotope. The targeting agent may be for example an antibody, an hapten or a peptide.

Above $H_2$Me-do2pa ligand does not enable the introduction of a bioactive group through a coupling function. The Applicant thus conducted research to enable functionalization of $H_2$Me-do2pa ligand.

The main concern when introducing a coupling function or a bioactive group on a chelating agent is to retain its physicochemical properties. In the present case, complexation dual competence to lead and bismuth should especially be retained. Moreover, the bifunctional chelating agent should also retain rapid metallation kinetics with respect to the time of the radionuclide half-life; kinetic inertness; solubility in aqueous media, especially in physiological media; and in vivo stability.

Another concern when searching to functionalize $H_2$Me-do2pa ligand was to provide a versatile synthesis process enabling wide possibilities of functionalization. Especially, selective reactions together with original protection/deprotection methods were developed.

The present invention thus provides new bifunctional chelating agents having complexation dual competence to lead and bismuth, which are functionalizable or functionalized with a bioactive group, while meeting above specifications required for optimized chelates intended to be used in nuclear medicine. Ligands of the invention are of general formula (I):

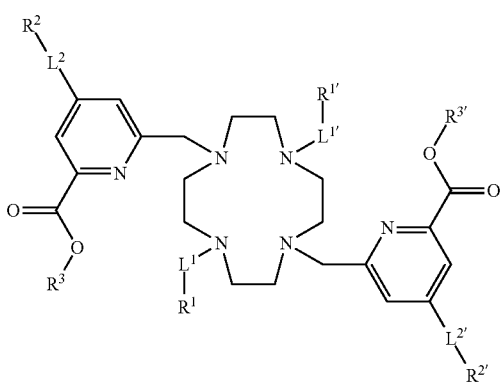

(I)

wherein $R^1$, $R^{1'}$, $R^2$, $R^{2'}$, $R^3$, $R^{3'}$, $L^1$, $L^{1'}$, $L^2$ and $L^{2'}$ are as defined below.

The structure of the ligands of formula (I) of the invention enables bio-vectorization by the introduction of bioactive groups through N-functionalization and/or by functionalization of the picolinate arm.

The ligand of formula (I) of the invention presents the advantage of being easily manufactured.

Upon complexation with metallic cations, the ligands of the invention lead to chelates meeting the requirements of the above specifications.

Moreover, further to $^{212}$Bi and $^{213}$Bi, the ligands of the invention present a good affinity for other radioisotopes useful in nuclear medicine, such as for example $^{64}$Cu, $^{67}$Cu, $^{68}$Ga, $^{89}$Zr, $^{99m}$Tc, $^{111}$In, $^{186}$Re, $^{188}$Re, $^{211}$At, $^{225}$Ac, $^{90}$Y $^{177}$Lu, $^{153}$Sm, $^{149}$Tb or $^{166}$Ho.

Besides applications in nuclear medicine, the ligands of formula (I) of the invention may be used for epuration of effluents contaminated with radioactive elements or metals such as lead; catalysis; solid/liquid extraction and liquid/liquid extraction; or detection of traces of metallic cations.

Definitions

The terms "complex" or "chelate" refer to a molecule binding a metal ion. Chelation (or complexation) involves the formation or presence of two or more separate coordinate bonds between a polydentate (multiple bonded) molecule and a single central atom. Polydentate molecules are often organic compounds, and are called ligands, chelants, chelatants, chelators, chelating agents, or sequestering agents.

The terms "ligand" or "chelator" or "chelating agent" refer to a polydentate molecule able to form coordination bonds with a metal ion to give a chelate.

The term "coupling function" refers to a function capable to react with another function to form a covalent bond, i.e. is covalently reactive under suitable reaction conditions, and generally represents a point of attachment for another substance. The coupling function is a moiety on the compounds of the present invention that is capable of chemically reacting with a functional group on a different compound to form a covalent linkage. Coupling functions generally include nucleophiles, electrophiles and photoactivable groups.

In a preferred embodiment of the invention, the coupling function is selected from the group comprising amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromoacetamide or iodoacetamide; glutamate; glutaric anhydride, succinic anhydride, maleic anhydride; aldehyde; ketone; hydrazide; chloroformate and maleimide.

The term "activating function" refers to a chemical moiety capable to render reactive a chemical function. For example, for a carboxylic acid chemical function, an activating function may be N-hydroxysuccinimide, N-hydroxyglutarimide, maleimide, halide or anhydride moieties.

The term "activated carboxylic acid" refers for example to acid anhydride or acyl halide.

The term "activated ester" refers to an ester in which the alkoxy group is replaced by an electron-withdrawing group; examples of activated esters are N-hydroxysuccinimide ester, N-hydroxyglutarimide ester, N-hydroxybenzotriazole ester, maleimide ester or pentafluorophenyl ester.

The term "bioactive group" refers to a molecule being able to recognize a predefined biological target. Preferably, "bioactive group" refers to biomolecules, organic compounds or nanocarriers. "Biomolecules" include antibodies, peptides, proteins, lipids, polysaccharide, fatty acid, hapten, liposome, and polyamine; selected to bind biological targets. "Organic compounds" include fluorophores, chromophores and macrocyclic chelates. "Nanocarriers" include solid supports.

Bioactive groups and biological targets of interest are illustrated by the examples below:

| Bioactive group type | Biological target | Bioactive group family | Examples of bioactive group |
|---|---|---|---|
| antibody | CD20 | anti CD20 | Tositumomab (BEXXAR), ibritumumab tiuxetan (Zevalin) Rituximab, Ofatumumab |
| antibody | CEA | anti CEA | IMMU-4, arcitumomab, M5A, T84, 2A3, 2A3-mFc, 9A6 (*Journal of Controlled Release*, May 2012; 161(1): 18-24.); WO 2012/040824 |
| peptide | gastrin-releasing peptide (GRP) receptors | Bombesin, derivatives and analogs of bombesin | PEG4-Bombesin (*D. WILD, Canc. Res.,* 2011; *S. DäPP, Eur J Nucl Med,* 2012), Bombesin, -[D-Tyr$^6$, βAla$^{11}$, Thi$^{13}$, Nle$^{14}$]bombesin, PEG$_2$-[D-Tyr$^6$, βAla$^{11}$, Thi$^{13}$, Nle$^{14}$]bombesin, -4-amino-1-carboxymethyl-piperidine-D-Phe-Gln-Trp-Ala-Val-Gly-His-Sta-Leu-NH$_2$, D-Phe-Gln-Trp-Ala-Val-Gly-His-Sta-Leu-NH$_2$, RGD-BBN |
| antibody | HER2 | anti HER2 | ZHER2: 342 (*J Nucl Med* 2009; 50: 417-425), ZHER2: 2891, ZHER2: 2395, ZHER2: 2891-ABD035 and derivatives (*J Nucl Med.* 2010; 51: 1131-1138; *J Nucl Med.* 2013 June; 54(6): 961-8.), ABY-025, ABY-028 and derivatives |
| antibody | EGFR | anti EGFR | Cetuximab, panitumumab, L19-SIP |
| peptide | somatostatin receptors | somatostatin analogs | OCTREOTIDE, TATE, TOC, octreotate, 1-Nal$^3$-octreotide (NOC), lanreotide, p-Cl-Phe-cyclo(D-Cys-Tyr-D-Aph(Cbm)-Lys-Thr-Cys)D-Tyr-NH$_2$ (LM3), p-NO$_2$-Phe-cyclo(D-Cys-Tyr-D-Aph(Cbm)-Lys-Thr-Cys)D-Tyr-NH$_2$ (JR10), Cpa-cyclo(D-Cys-Tyr-D-Aph(Cbm)-Lys-Thr-Cys)D-Tyr-NH$_2$, pansomatostatin |
| peptide | alphavbeta3 integrin | RGD peptides | Cyclo-RGD (*GAERTNER, Eur. J. Nucl. Med,* 2012), RGD tetramer (CHENG, *Eur J. Nucl. Med,* 2011) |
| minibody | PSMA - prostate | Anti-PSMA | HuJ591 minibody |
| mAb | PSMA - prostate | Anti-PSMA | J591, WO2011/069019, 7E11 |
| small molecule | carboxypeptidase of PSMA | urea-based inhibitors | Lys-urea-Asp sequence (CHEN et al., Clin Cancer Res 2011) and derivatives thereof |
| small molecule | Bones | Bone mineralization | Phosphonates, biphosphonates |
| peptide | cholecystokinin 2 receptors (CCK) | CCK analogs | minigastrin (Roosenburg et al., Amino Acids 2010; von Guggenberg et al., Mol Imaging 2012; Brom et al., Mol Imaging 2011) |
| peptide | melanocortin-1 receptor | α-MSH analogs | [Ser-Tyr-Ser-Met-Glu-His-Phe-Arg-Trp-Gly-Lys-Pro-Val]-NH$_2$ (H. Guo, J. Nucl Med, 2010; T. Quinn et al., G Ital Dermatol Venereol 2010) |
| small molecules | melanocortin-1 receptor | benzamide derivatives | benzamides derivatives (A. Maisonial, J Med Chem, 2011, Billaud et al., J Med Chem, 2013) |
| peptide | NK1-receptor - glioblastoma | neuropeptide | P substance Cordier et al, J Neurooncol 2010) |
| peptide | chemokine receptor 4 (CXCR4) | Chemokine analogs | fusine, CD 184, SDF-1a(CXCL12) (Liotta LA et al, Nature 2001; Gourni et al, J Nucl Med 2011)) |

The term "linker" refers to a single covalent bond or a moiety comprising series of stable covalent bonds, the moiety often incorporating 1-40 plural valent atoms selected from the group consisting of C, N, O, S and P, that covalently attach a coupling function or a bioactive group to the ligand of the invention. The number of plural valent atoms in a linker may be, for example, 0, 1, 2, 3, 4, 5, 6, 7, 8, 9, 10, 20, 25 or 30. A linker may be linear or non-linear; some linkers have pendant side chains or pendant functional groups (or both). Examples of such pendant moieties are hydrophilicity modifiers, for example solubilizing groups like, e.g. sulfo (—SO$_3$H or —SO$_3^-$) or carboxylate (—COO$^-$).

In one embodiment, a linker is composed of any combination of single, double, triple or aromatic carbon-carbon bonds, carbon-nitrogen bonds, nitrogen-nitrogen bonds, carbon-oxygen bonds and carbon-sulfur bonds. Linkers may by way of example consist of a combination of moieties selected from alkyl, —C(O)NH—, —C(O)O—, —NH—, —S—, —O—, —C(O)—, —S(O)$_n$— where n is 0, 1 or 2; 5- or 6-membered monocyclic rings and optional pendant functional groups, for example sulfo, hydroxy and carboxy.

The coupling function may be reacted with a substance reactive therewith, whereby the linker becomes bonded to a bioactive group. In this case, the linker typically contains a residue of a coupling function (such as for example the carbonyl group of an ester; the triazolo group resulting from a click reaction between an azide and an alkyne; the —NHC(=S)NH— group resulting from the coupling of an amine on an isothiocyanate function).

Where chemical substituents are combinations of chemical groups, the point of attachment of the substituent to the molecule is by the last chemical group recited. For example, an arylalkyl substituent is linked to the rest of the molecule through the alkyl moiety and it may be represented as follows: "aryl-alkyl-".

The term "alkyl" refers to any saturated linear or branched hydrocarbon chain, with 1 to 12 carbon atoms, preferably 1 to 6 carbon atoms, and more preferably methyl, ethyl, n-propyl, i-propyl, n-butyl, i-butyl, s-butyl and t-butyl, pentyl and its isomers (e.g. n-pentyl, i-pentyl), and hexyl and its isomers (e.g. n-hexyl, i-hexyl).

The terms "alkene" or "alkenyl" refer to any linear or branched hydrocarbon chain having at least one double bond, of 2 to 12 carbon atoms, and preferably 2 to 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The terms "alkyne" or "alkynyl" refer to any linear or branched hydrocarbon chain having at least one triple bond, of 2 to 12 carbon atoms, and preferably 2 to 6 carbon atoms. Non limiting examples of alkynyl groups are ethynyl, 2-propynyl, 2-butynyl, 3-butynyl, 2-pentynyl and its isomers, 2-hexynyl and its isomers- and the like.

The term "amine" refers in the present invention to the group —NH$_2$ and to secondary amines —NHR wherein R is different from H, preferably wherein R is an alkyl group; preferably "amine" refers to —NH$_2$.

The term "aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylalkyl" refers to an alkyl group substituted by an aryle group: aryl-alkyl-.

The term "alkylaryl" refers to an aryl group substituted by an alkyl group: alkyl-aryl-.

The term "heteroaryl" refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno [3,2-b] furanyl, thieno [3,2-b] thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1(6H)-yl, 2-oxopyridin-1(2H)-yl, 6-oxopyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "heteroarylalkyl" refers to an alkyl group substituted by an aryle group: heteroaryl-alkyl-.

The term "alkylheteroaryl" refers to an aryl group substituted by an alkyl group: alkyl-heteroaryl-.

The term "siloxy" refers to the function —O—Si(R)$_3$ wherein R represents for example alkyl or aryl.

The term "thioether" refers to a functional group with the connectivity C—S—C.

The term "halide" refers to fluoro, chloro, bromo, or iodo. Preferred halo groups are chloro and bromo.

The term "oxoamine" refers to a —(C=O)—NH$_2$ group.

The term "aminooxy" refers to a —O—NH$_2$ group.

The term "ketone" refers to a functional group with the connectivity C—(C=O)—C.

The term "hapten" refers to a small molecule that can elicit an immune response only when attached to a large carrier.

The term "antibody" refers monoclonal antibodies (mAb), polyclonal antibodies, multispecific antibodies (e.g., bispecific antibodies), hybrid or chimeric antibodies and antibody fragments, so long as they exhibit the desired biological activity. An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules, especially single-chain variable fragment (scFv); and multispecific antibodies formed from antibody fragments.

The term "peptide" refers to a linear polymer of amino acids of less than 50 amino acids linked together by peptide bonds.

The term "protein" refers to a functional entity formed of one or more peptides.

The term "polysaccharide" refers to a polymeric carbohydrate molecule composed of long chains of monosaccharide units bound together by glycosidic linkages; which may be linear or branched. Examples include starch, glycogen, cellulose and chitin.

The term "fatty acid" refers to a carboxylic acid with a long aliphatic tail (chain), such as, for example, from 4 to 36 atoms of carbon, which is either saturated or unsaturated.

The term "liposome" refers to an artificial vesicle formed by concentric lipid bilayers, trapping therebetween aqueous compartments. A wide variety of amphiphilic lipids can be used to form liposomes, the most commonly used are the phospholipids.

The term "lipid" refers to hydrophobic or amphiphilic small molecules, which are naturally occurring and include fats, waxes, sterols, fat-soluble vitamins (such as vitamins A, D, E, and K), monoglycerides, diglycerides, triglycerides and phospholipids. Lipids may be divided into eight categories: fatty acids, glycerolipids, glycerophospholipids, sphingolipids, saccharolipids, polyketides (derived from condensation of ketoacyl subunits); sterol lipids and prenol lipids (derived from condensation of isoprene subunits).

The term "fluorophore" refers to a chemical substance able to emit fluorescent light after excitation. Preferably, fluorophores are molecules comprising several conjugated aromatic rings or planar cyclic molecules having one or more π bond. Examples of fluorophores are: coumarines (hydroxycoumarine, aminocoumarine, methoxycoumarine); fluoresceine, rhodamines (X-rhodamine, lissamine rhodamine B), cyanine derivatives (Cy3, Cy5). Fluorophores also comprise fluorescent proteines, such as for example GFP and derivatives thereof.

The term "radiopharmaceutical" refers to a radioactive medicinal product. Radiopharmaceuticals are used in the field of nuclear medicine for the treatment of many diseases and/or as tracers for their diagnosis.

The term "patient" refers to a warm-blooded animal, more preferably to a human, who/which is awaiting the receipt of, or is receiving medical care or is/will be the object of a medical procedure.

The term "treat", "treating" and "treatment", as used herein, are meant to include alleviating, attenuating or abrogating a condition or disease and/or its attendant symptoms.

The term "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient that is sufficient to achieve the desired therapeutic or prophylactic effect in the patient to which/whom it is administered.

The term "administration", or a variant thereof (e.g. "administering"), means providing the active agent or active ingredient, alone or as part of a pharmaceutically acceptable composition, to the patient in whom/which the condition, symptom, or disease is to be treated or prevented.

The term "pharmaceutically acceptable" means that the ingredients of a pharmaceutical composition are compatible with each other and not deleterious to the patient thereof.

DETAILED DESCRIPTION

Ligand

This invention relates to a bifunctional do2pa derivative ligand of formula (I):

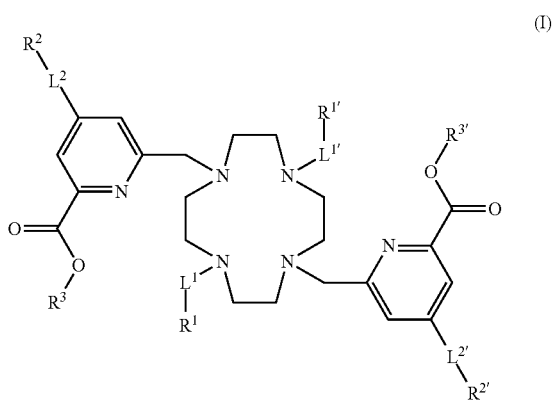

(I)

wherein
$R^1$, $R^{1'}$, $R^2$ and $R^{2'}$ each independently represents:
  a hydrogen atom;
  a coupling function, wherein the coupling function is selected from amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromoacetamide or iodoacetamide; glutamate; glutaric anhydride, succinic anhydride, maleic anhydride; aldehyde; ketone; hydrazide; chloroformate and maleimide;
  a bioactive group, wherein the bioactive group is selected from antibody, such as polyclonal or monoclonal antibody, hybrid or chimeric antibody, single-domain antibody, dimeric or trimeric antibody fragment construct or minibody; hapten; peptide; protein; polysaccharide; fatty acid; liposome; lipid; polyamine such as spermine; solid support such as nanoparticle or polymeric microparticle; fluorophore; chromophore; macrocyclic chelate; and combination thereof,
$L^1$, $L^{1'}$, $L^2$ and $L^{2'}$ each independently represents:
  a single bond;
  a linker selected from alkyl, aryl, arylalkyl, alkylaryl, heteroaryl, heteroarylalkyl, alkylheteroaryl, alkenyl, alkynyl, wherein alkyl moieties are optionally interrupted by one or more heteroatoms selected from O, N and S; optionally additionally comprising a residue of a coupling function through which $R^1$, $R^{1'}$, $R^2$ and $R^{2'}$ are bounded to $L^1$, $L^{1'}$, $L^2$ and $L^{2'}$ respectively;
$R^3$ and $R^{3'}$ each independently represents:
  a hydrogen atom;
  an activating function, wherein the activating function is selected from N-hydroxysuccinimide, N-hydroxyglutarimide, maleimide, halide and —OCOR$^4$, wherein $R^4$ is selected from alkyl, aryl;

a bioactive group, wherein the bioactive group is selected from antibody, such as polyclonal or monoclonal antibody, hybrid or chimeric antibody, single-domain antibody, dimeric or trimeric antibody fragment construct or minibody; hapten; peptide; protein; polysaccharide; fatty acid; liposome; lipid; polyamine such as spermine; solid support such as nanoparticle or polymeric microparticle; fluorophore; chromophore; macrocyclic chelate; and combination thereof, provided that at least one of -$L^1$-$R^1$, -$L^{1'}$-$R^{1'}$, -$L^2$-$R^2$ and -$L^{2'}$-$R^{2'}$ represents a linker with a coupling function or a linker with a bioactive group.

In one embodiment, $R^3$ and $R^{3'}$ are both hydrogen atoms.

In one embodiment, -$L^2$-$R^2$ and -$L^{2'}$-$R^{2'}$ represent both hydrogen atoms.

In one embodiment, in formula (I), at least one of -$L^1$-$R^1$, -$L^{1'}$-$R^{1'}$, -$L^2$-$R^2$ and -$L^{2'}$-$R^{1'}$ is selected from formulae (a) and (b):

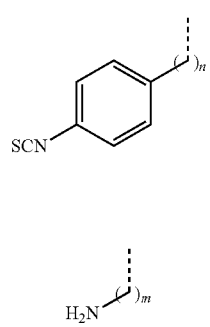

(a)

(b)

wherein n and m represent each independently an integer ranging from 1 to 10, preferably 1, 2, 3 or 4.

According to an embodiment, preferred ligands of formula (I) are of formula (Ia):

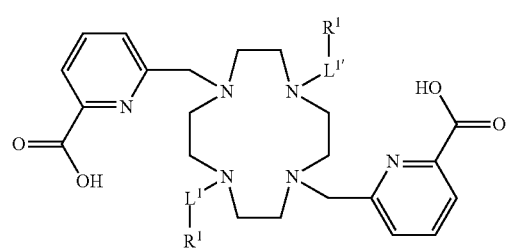

(Ia)

wherein $R^1$, $R^{1'}$, $L^1$ and $L^{1'}$ are as defined in formula (I).

According to one embodiment, in formula (Ia), $L^{1'}$ is an alkyl linker and $R^1$ is a hydrogen atom.

According to an embodiment, preferred ligands of formula (Ia) are of formula (Ib):

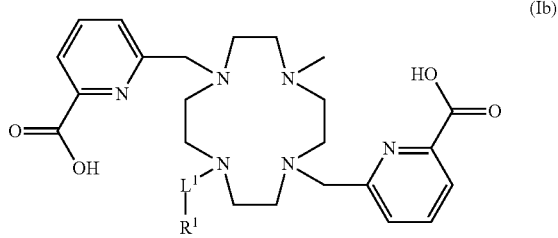

(Ib)

wherein $R^1$ and $L^1$ are as defined in formula (I).

According to a specific embodiment, in formulae (Ia) and (Ib), -$L^1$-$R^1$ is selected from formulae (a) and (b):

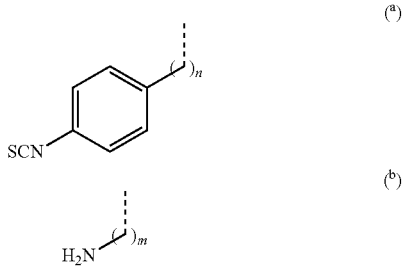

(a)

(b)

wherein n and m represent each independently an integer ranging from 1 to 10, preferably 1, 2, 3 or 4.

According to a specific embodiment, in formulae (Ia) and (Ib), -$L^1$-$R^1$ is selected from formulae (a1) and (b1):

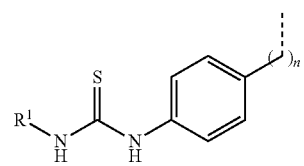

(a1)

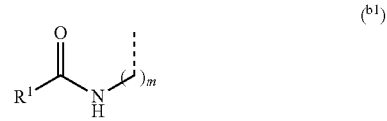

(b1)

wherein n and m represent each independently an integer ranging from 1 to 10, preferably 1, 2, 3 or 4; and $R^1$ is as defined in formula (I), preferably $R^1$ is a bioactive group, more preferably $R^1$ is a hapten group.

According to a specific embodiment, the ligand of formula (I) of the invention is grafted on nanoparticles.

Particularly preferred compounds of formula (I) of the invention are those listed in Table 1 hereafter:

TABLE 1

| Cpd no | Structure | Chemical name |
|---|---|---|
| I-1 | 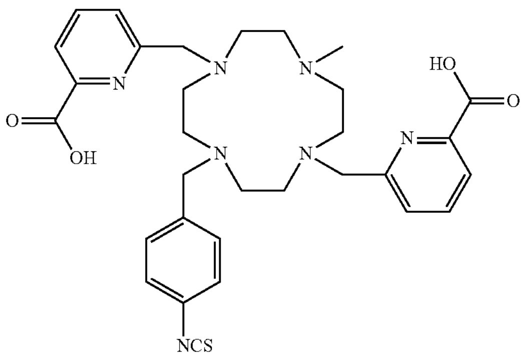 | 6,6'-((4-(4-isothiocyanatobenzyl)-10-methyl-1,4,7,10-tetraazacyclododecane-1,7-diyl)bis(methylene))dipicolinic acid |
| I-2 | 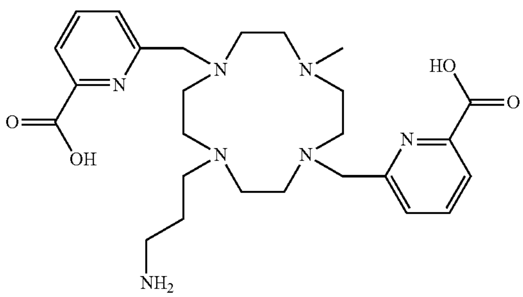 [SMILES: CN1CCN(Cc2cccc(C(=O)O)n2)CCN(CCCN)CCN(Cc2cccc(C(=O)O)n2)CC1] | 6,6'-((4-(3-aminopropyl)-10-methyl-1,4,7,10-tetraazacyclododecane-1,7-diyl)bis(methylene))dipicolinic acid |
| I-3 | 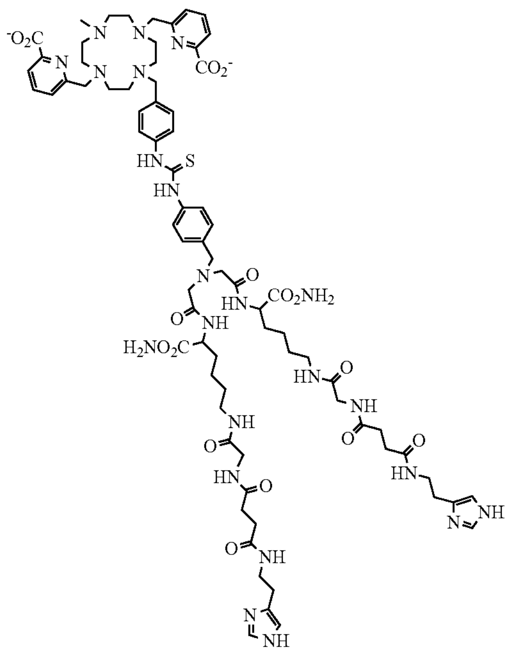 | 6,6'-((4-(4-(3-(4-(6-((aminooxy)carbonyl)-2-(16-((aminooxy)carbonyl)-1-(1H-imidazol-4-yl)-4,7,10,18-tetraoxo-3,8,11,17-tetraazanonadecan-19-yl)-21-(1H-imidazol-4-yl)-4,12,15,18-tetraoxo-2,5,11,14,19-pentaazahenicosyl)phenyl)thioureido)benzyl)-10-methyl-1,4,7,10-tetraazacyclododecane-1,7-diyl)bis(methylene))dipicolinate |

In Table 1, the term "Cpd" means compound.

The compounds of Table 1 were named using ChemBioDraw® Ultra version 12.0 (PerkinElmer).

Chelate

The present invention further relates to a chelate resulting from the complexation of a ligand of the invention of formula (I) as described above and a metallic cation, preferably lead (II) or bismuth (III). In one embodiment, the metallic cation is selected from the group consisting of Pb (II) and Bi(III).

Unless otherwise stated Pb (II) and Bi(III) encompass their radioactive isotopes, such as $^{212}$Pb, $^{212}$Bi and $^{213}$Bi.

In an embodiment, the present invention relates to a chelate resulting from the complexation of a ligand of formula (I)

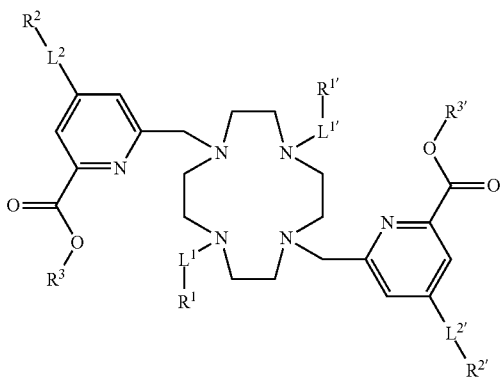

(I)

wherein

R¹, R¹', R² and R²' each independently represents:
- a hydrogen atom;
- a coupling function, wherein the coupling function is selected from amine; isothiocyanate; isocyanate; activated ester such as for example N-hydroxysuccinimide ester, N-hydroxyglutarimide ester or maleimide ester; carboxylic acid; activated carboxylic acid such as for example acid anhydride or acid halide; alcohol; alkyne; halide; azide; siloxy; phosphonic acid; thiol; tetrazine; norbornen; oxoamine; aminooxy; thioether; haloacetamide such as for example chloroacetamide, bromoacetamide or iodoacetamide; glutamate; glutaric anhydride, succinic anhydride, maleic anhydride; aldehyde; ketone; hydrazide; chloroformate and maleimide;
- a bioactive group, wherein the bioactive group is selected from antibody, such as polyclonal or monoclonal antibody, hybrid or chimeric antibody, single-domain antibody, dimeric or trimeric antibody fragment construct or minibody; hapten; peptide; protein; polysaccharide; fatty acid; liposome; lipid; polyamine such as spermine; solid support such as nanoparticle or polymeric microparticle; fluorophore; chromophore; macrocyclic chelate; and combination thereof, $L^1$, $L^{1'}$, $L^2$ and $L^{2'}$ each independently represents:
- a single bond;
- a linker selected from alkyl, aryl, arylalkyl, alkylaryl, heteroaryl, heteroarylalkyl, alkylheteroaryl, alkenyl, alkynyl, wherein alkyl moieties are optionally interrupted by one or more heteroatoms selected from O, N and S; optionally additionally comprising a residue of a coupling function through which $R^1$, $R^{1'}$, $R^2$ and $R^{2'}$ are bounded to $L^1$, $L^{1'}$, $L^2$ and $L^{2'}$ respectively;

$R^3$ and $R^{3'}$ each independently represents:
- a hydrogen atom;
- an activating function, wherein the activating function is selected from N-hydroxysuccinimide, N-hydroxyglutarimide, maleimide, halide and —OCOR⁴, wherein R⁴ is selected from alkyl, aryl;
- a bioactive group, wherein the bioactive group is selected from antibody, such as polyclonal or monoclonal antibody, hybrid or chimeric antibody, single-domain antibody, dimeric or trimeric antibody fragment construct or minibody; hapten; peptide; protein; polysaccharide; fatty acid; liposome; lipid; polyamine such as spermine; solid support such as nanoparticle or polymeric microparticle; fluorophore; chromophore; macrocyclic chelate; and combination thereof, provided that at least one of -L¹-R¹, -L¹'-R¹', -L²-R² and -L²'-R²' represents a linker with a coupling function or a linker with a bioactive group;

with a metallic cation selected from bismuth (III), lead (II), copper (II), copper (I), gallium (III), zirconium (IV), technetium (III), indium (III), rhenium (VI), astatine (III), yttrium (III), samarium (III), actinium (III), lutetium (III), terbium (III), holmium (III), gadolinium (III), europium(III); preferably selected from bismuth (III) and lead (II).

According to a preferred embodiment, the metallic cation is a radioisotope, preferably a radioisotope selected from $^{212}$Bi ($^{212}$Pb), $^{213}$Bi(III), $^{64}$Cu(II), $^{67}$Cu(II), $^{68}$Ga(III), $^{89}$Zr (IV), $^{99m}$Tc(III), $^{111}$In(III), $^{186}$Re(VI), $^{188}$Re(VI), $^{211}$At(III), $^{225}$Ac(III), $^{90}$Y(III), $^{177}$Lu(III), $^{153}$Sm(III), $^{149}$Tb(III) or $^{166}$Ho(III), more preferably $^{212}$Bi ($^{212}$Pb), $^{213}$Bi(III).

According to a preferred embodiment, the metallic cation is a radioisotope, preferably the metallic cation is the in situ $^{212}$Pb/$^{212}$Bi generator, more preferably the metallic cation is $^{212}$Pb.

When the metallic cation is a radioisotope, the chelate of the invention is a radiopharmaceutical.

Preferred embodiments relative to the ligand of formula I described above apply to the chelate of the invention.

According to one embodiment, the ligand and/or the chelate of the invention may be grafted on solid support, such as for example nanoparticles, preferably gold, iron, or quantum dots According to one embodiment, the ligand and/or the chelate of the invention may be grafted on solid support, such as for example silicium, alumine or resin.

According to one embodiment, the ligand and/or the chelate of the invention may be linked to other ligands/chelates, such as for example porphyrines, cyclodextrines, calixarenes or azacycloalkanes. In this case, the resulting chelate may be used for bimodal imaging or for theragnostic.

Process of Manufacturing—Ligand and Chelate

The present invention further relates to a process for manufacturing the ligand of the invention. According to one embodiment, the ligand of formula (I) may be obtained starting from cyclen glyoxal:

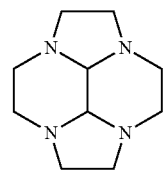 [SMILES: C1CN2CCN3CCN4CCN1C2C43]

Starting from cyclen glyoxal, pendant arms -L¹-R¹ and -L¹'-R¹' may first be introduced (steps (a1) and (a1')), followed by picolinate arms (steps (b1) and (b1')) or alternatively, picolinate arms may first be introduced (steps (b1) and (b1')) before pendant arms -L¹-R¹ and -L¹'-R¹' (steps (a1) and (a1')). In both cases, a deprotection step of the glyoxal bridge (step (c)) should be performed after the functionalization of the 2 first amines and before the functionalization of the 2 remaining amines. These synthesis routes are summarized in the scheme below:

17
18
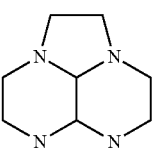
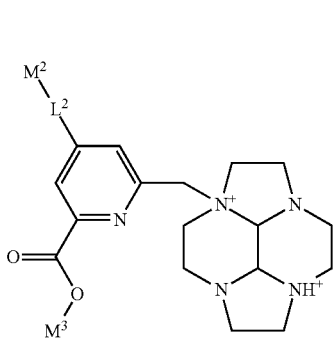 (b1)
(a1) 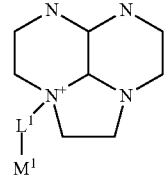
iii
(b1′) ↓
↓ (a′1)
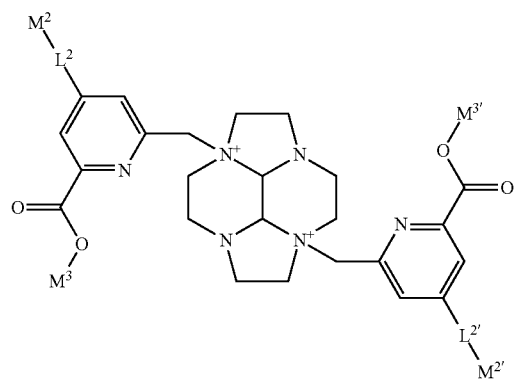
vi′
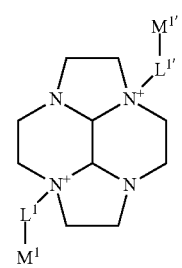
iii′
↓ (c)
↓ (c)
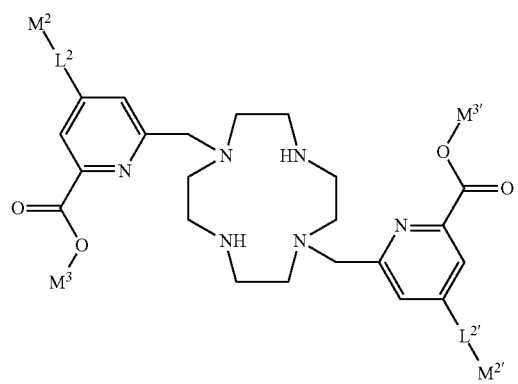
vii
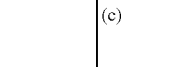
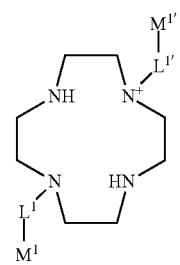
iv
↓ (a1)
↓ (b1)
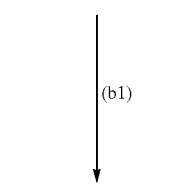

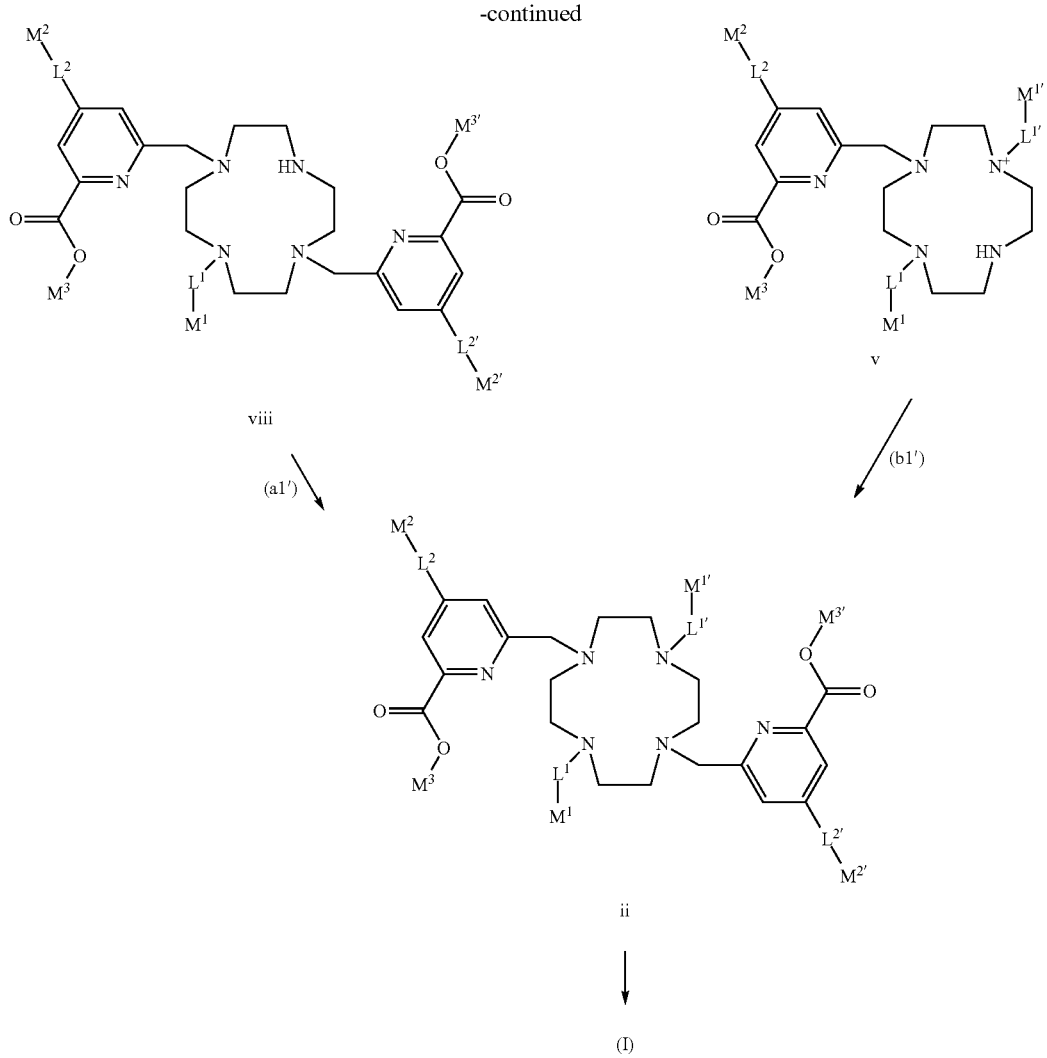

Therefore, according to one embodiment, the process for manufacturing the ligand of formula (I) of the invention comprises starting from cyclen glyoxal:

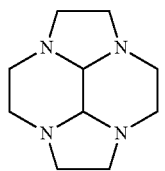 [SMILES: C1CN2CCN3CCN4CCN1C2C43]

and performing the following steps:
(a1) reacting with compound $M^1$-$L^1$-$X^1$ wherein
  $L^1$ is as defined in formula (I);
  $X^1$ represents a halogen atom, preferably Br or I;
  $M^1$ represents $R^1$, wherein $R^1$ is as defined in formula (I); or $M^1$ represents a precursor of a coupling function;
(a1') reacting with compound $M^{1'}$-$L^{1'}$-$X^{1'}$ wherein
  $L^{1'}$ is as defined in formula (I);
  $X^{1'}$ represents a halogen atom, preferably Br or I;
  $M^{1'}$ represents $R^{1'}$, wherein $R^{1'}$ is as defined in formula (I); or $M^{1'}$ represents a precursor of a coupling function;
(b1) reacting with compound of formula (i)

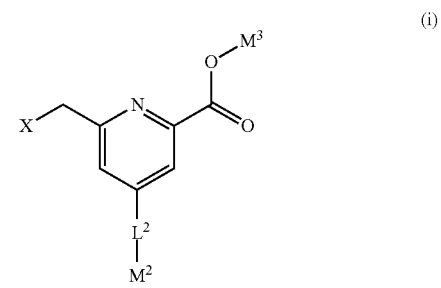

wherein
  $L^2$ is as defined in formula (I);
  X represents a halogen atom, preferably Cl;
  $M^2$ represents $R^2$, wherein $R^2$ is as defined in formula (I); or $M^2$ represents a precursor of a coupling function;

M³ represents
  a protecting group selected from alkyl group, preferably methyl, ethyl or t-butyl, more preferably methyl; or
  R³, wherein R³ is as defined in formula (I), provided that it does not represents a hydrogen atom;
(b1') reacting with compound of formula (i')

(i')

wherein
  L²' is as defined in formula (I);
  X represents a halogen atom, preferably Cl;
  M²' represents R²', wherein R²' is as defined in formula (I); or M² represents a precursor of a coupling function;
  M³' represents
    a protecting group selected from alkyl group, preferably methyl, ethyl or t-butyl, more preferably methyl; or
    R³', wherein R³' is as defined in formula (I), provided that it does not represents a hydrogen atom;
(c) performing glyoxal bridge deprotection;
said steps being performed in the following order: (a1), (a1'), (c), (b1) and (b1'); or alternatively (b1), (b1'), (c), (a1) and (a1');
to afford intermediate compound (ii)

(ii)

wherein $L^1$, $L^{1'}$, $L^2$, $L^{2'}$ are as defined in formula (I) and wherein $M^1$, $M^{1'}$, $M^2$, $M^{2'}$, $M^3$ and $M^{3'}$, are as defined above;
and where needed, conducting on intermediate compound (ii) one or more subsequent step selected from:
  in the case wherein $M^1$, $M^{1'}$, $M^2$ or $M^{2'}$ represents a precursor of a coupling function, converting the precursor to a coupling function to afford compound of formula (I) wherein $R^1$, $R^{1'}$, $R^2$ or $R^{2'}$ respectively represents a coupling function;
  in the case wherein $M^1$, $M^{1'}$, $M^2$ or $M^{2'}$ represents a coupling function, introducing a bioactive group to afford compound of formula (I) wherein $R^1$, $R^{1'}$, $R^2$ or $R^{2'}$ respectively represents a bioactive group;
  in the case wherein $M^3$ or $M^{3'}$ represents a protecting group, deprotecting the acidic function, to afford compound of formula (I) wherein $R^3$ or $R^{3'}$ represent a hydrogen atom;
  introducing an activating function or a bioactive group on the acidic function to afford compound of formula (I) wherein $R^3$ or $R^{3'}$ represents an activating function or a bioactive group;
  to afford compound of formula (I).

In the present invention a "precursor of a coupling function" refers to a coupling function with a protective group or to a chemical moiety which may be interconverted to afford a coupling function. An example of a coupling function with a protective group is a protected amine group, wherein the amino-protecting group is of common knowledge for a person skilled in the art, such as for example a Boc or a Fmoc group. An example of chemical moiety which may be interconverted to afford a coupling function is a nitro group, which may be converted into amine or even into isothiocyanate coupling function.

According to one embodiment, step (c) of deprotection of the glyoxal bridge may be performed using hydrazine hydrate or ethylenediamine.

According to a preferred embodiment, step (c) of deprotection of the glyoxal bridge is performed using ethylenediamine. Preferably, deprotection using ethylenediamine is performed in mild conditions. Especially, deprotection may be performed in a solvent such as dichloromethane. Moreover, deprotection is preferably performed at room temperature.

When pendent arms $-L^1-M^1$ and $L^{1'}-M^{1'}$ are different or when picolinate arms are different, the first substitution of cyclen glyoxal, through step (a1) or (b1), should be controlled in order to obtain the mono-substituted intermediate (iii) or (vi). In a preferred embodiment, reaction of cyclen glyoxal through step (a1) or (b1) is conducted in THF to favor mono-addition, leading to the precipitation of intermediate (iii) or (vi) respectively; and the second arm is introduced through step (a1') or (b1'), using acetonitrile as solvent, leading to intermediate (iii') or (vi'). In one embodiment, intermediate (iii) or (vi) is not further purified before undergoing step (a1') or (b1'), respectively.

When pendent arms $-L^1-M^1$ and $L^{1'}-M^{1'}$ are identical or when picolinate arms are identical, the substitution of cyclen glyoxal, through step (a1) or (b1) is performed in presence of an excess of reactant, to afford directly intermediate (iii') or (vi'), respectively. Preferably, an excess of more than 2 molar equivalents is used, more preferably from 2 to 4 equivalents.

When picolinate arms are different or when pendent arms $-L^1-M^1$ and $L^{1'}-M^{1'}$ are different, the first substitution of deprotected intermediate (iv) or (vii), through step (b1) or (a1), should be controlled in order to obtain the mono-substituted intermediate (v) or (viii). Mono-substitution is favored by using 1 equivalent of reactant. Preferably, the more bulky arm is first introduced, so that the steric hindrance favor the mono-addition. In one embodiment, intermediate (v) or (viii) is purified before undergoing step (b1') or (a1'), respectively, preferably by column chromatography.

When picolinate arms are identical or when pendent arms $-L^1-M^1$ and $L^{1'}-M^{1'}$ are identical, the substitution of deprotected intermediate (iv) or (vii), through step (b1) or (a1) is performed in presence of an excess of reactant, to afford directly intermediate (ii). Preferably, an excess of more than 2 molar equivalents is used, more preferably from 2 to 4 equivalents.

In the case wherein pendent arms -$L^1$-$M^1$ and $L^{1'}$-$M^{1'}$ are different and picolinate arms are different, synthesis of intermediate (ii) may be performed either by steps (a1), (a1'), (c), (b1) and (b1') or alternatively by steps (b1), (b1'), (c), (a1) and (a1').

In the case wherein pendent arms -$L^1$-$M^1$ and $L^{1'}$-$M^{1'}$ are different and picolinate arms are identical, synthesis of intermediate (ii) is preferably performed in the following order: (a1), (a1'), (c), (b1).

In the case wherein pendent arms -$L^1$-$M^1$ and $L^{1'}$-$M^{1'}$ are identical and picolinate arms are different, synthesis of intermediate (ii) is preferably performed in the following order: (b1), (b1'), (c), (a1).

In the case wherein pendent arms -$L^1$-$M^1$ and $L^{1'}$-$M^{1'}$ are identical and picolinate arms are identical, synthesis of intermediate (ii) may be performed either by steps (a1), (c) and (b1) or alternatively by steps (b1), (c) and (a1).

According to a first embodiment, the process for manufacturing the ligand of formula (I) of the invention comprises reacting cyclen glyoxal:

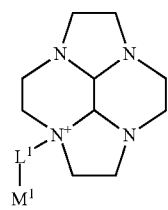

(a1) with compound $M^1$-$L^1$-$X^1$ wherein $L^1$ is as defined in formula (I);

$X^1$ represents a halogen atom, preferably Br or I;

$M^1$ represents $R^1$, wherein $R^1$ is as defined in formula (I); or $M^1$ represents a precursor of a coupling function;

to afford compound (iii)

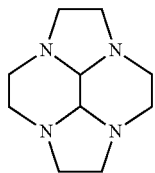

wherein $L^1$ and $M^1$ are as defined above;

(a1') reacting (iii) with compound $M^{1'}$-$L^{1'}$-$X^{1'}$ wherein $L^{1'}$ is as defined in formula (I);

$X^{1'}$ represents a halogen atom, preferably Br or I;

$M^{1'}$ represents $R^{1'}$, wherein $R^{1'}$ is as defined in formula (I); or $M^{1'}$ represents a precursor of a coupling function;

to afford compound (iii')

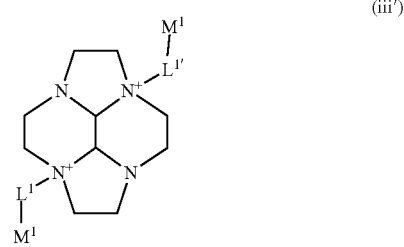

wherein $L^1$, $L^{1'}$, $M^1$ and $M^{1'}$ are as defined above;

(c) deprotecting glyoxal bridge of compound (iii'), to afford compound (iv)

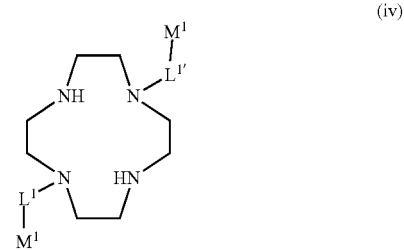

wherein $L^1$, $L^{1'}$, $M^1$ and $M^{1'}$ are as defined above;

(b1) reacting (iv) with compound of formula (i)

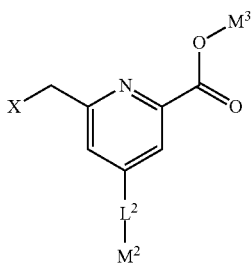

wherein $L^2$ is as defined in formula (I);

X represents a halogen atom, preferably Cl;

$M^2$ represents $R^2$, wherein $R^2$ is as defined in formula (I); or $M^2$ represents a precursor of a coupling function;

$M^3$ represents a protecting group selected from alkyl group, preferably methyl, ethyl or t-butyl, more preferably methyl; or $R^3$, wherein $R^3$ is as defined in formula (I), provided that it does not represents a hydrogen atom;

to afford compound (v)

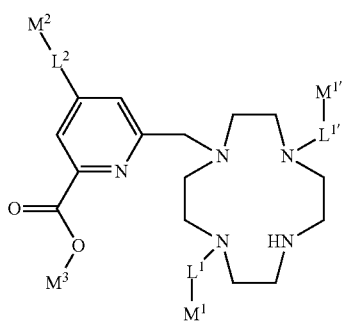

(v)

wherein L$^1$, L$^{1'}$ L$^2$ are as defined in formula (I) and wherein M$^1$, M$^{1'}$, M$^2$, M$^3$ are as defined above;

(b1') reacting (v) with compound of formula (i')

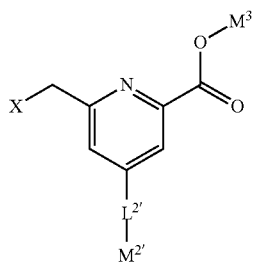

(i')

wherein
- L$^{2'}$ is as defined in formula (I);
- X represents a halogen atom, preferably Cl;
- M$^{2'}$ represents R$^{2'}$, wherein R$^{2'}$ is as defined in formula (I); or M$^{2'}$ represents a precursor of a coupling function;
- M$^{3'}$ represents
  - a protecting group selected from alkyl group, preferably methyl, ethyl or t-butyl, more preferably methyl; or
  - R$^{3'}$, wherein R$^{3'}$ is as defined in formula (I), provided that it does not represents a hydrogen atom;

to afford intermediate compound (ii)

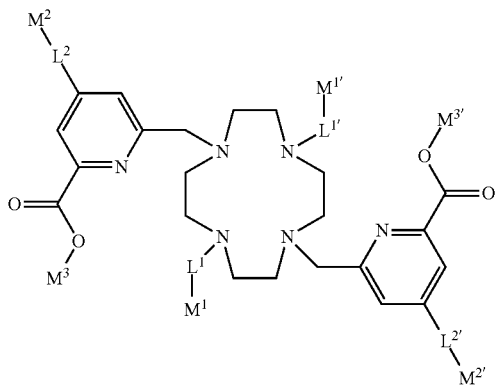

(ii)

wherein L$^1$, L$^{1'}$ L$^2$, L$^{2'}$ are as defined in formula (I) and wherein M$^1$, M$^{1'}$, M$^2$, M$^{2'}$, M$^3$ and M$^{3'}$, are as defined above;

and where needed, conducting on intermediate compound (ii) one or more subsequent step selected from:

- in the case wherein M$^1$, M$^{1'}$, M$^2$ or M$^{2'}$ represents a precursor of a coupling function, converting the precursor to a coupling function to afford compound of formula (I) wherein R$^1$, R$^{1'}$, R$^2$ or R$^{2'}$ respectively represents a coupling function;
- in the case wherein M$^1$, M$^{1'}$, M$^2$ or M$^{2'}$ represents a coupling function, introducing a bioactive group to afford compound of formula (I) wherein R$^1$, R$^{1'}$, R$^2$ or R$^{2'}$ respectively represents a bioactive group;
- in the case wherein M$^3$ or M$^{3'}$ represents a protecting group, deprotecting the acidic function, to afford compound of formula (I) wherein R$^3$ or R$^{3'}$ represent a hydrogen atom;
- introducing an activating function or a bioactive group on the acidic function to afford compound of formula (I) wherein R$^3$ or R$^{3'}$ represents an activating function or a bioactive group;

to afford compound of formula (I).

According to a second embodiment, the process for manufacturing the ligand of formula (I) of the invention comprises reacting cyclen glyoxal:

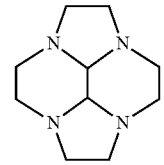 [SMILES: C1CN2CCN3CCN4CCN1C2C43]

(b1) with compound of formula (i)

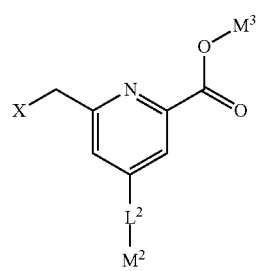

(i)

wherein
- L$^2$ is as defined in formula (I);
- X represents a halogen atom, preferably Cl;
- M$^2$ represents R$^2$, wherein R$^2$ is as defined in formula (I); or M$^2$ represents a precursor of a coupling function;
- M$^3$ represents
  - a protecting group selected from alkyl group, preferably methyl, ethyl or t-butyl, more preferably methyl; or
  - R$^3$, wherein R$^3$ is as defined in formula (I), provided that it does not represents a hydrogen atom;

to afford compound (vi)

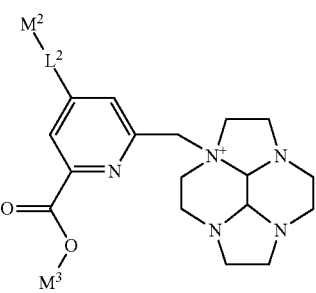

(vi)

wherein L² is as defined in formula (I) and wherein M² and M³ are as defined above;
(b1') reacting (vi) with compound of formula (i')

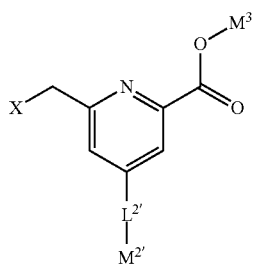

(i')

wherein
- L²' is as defined in formula (I);
- X represents a halogen atom, preferably Cl;
- M²' represents R²', wherein R²' is as defined in formula (I); or M² represents a precursor of a coupling function;
- M³' represents
  - a protecting group selected from alkyl group, preferably methyl, ethyl or t-butyl, more preferably methyl; or
  - R³', wherein R³' is as defined in formula (I), provided that it does not represents a hydrogen atom;

to afford intermediate compound (vi')

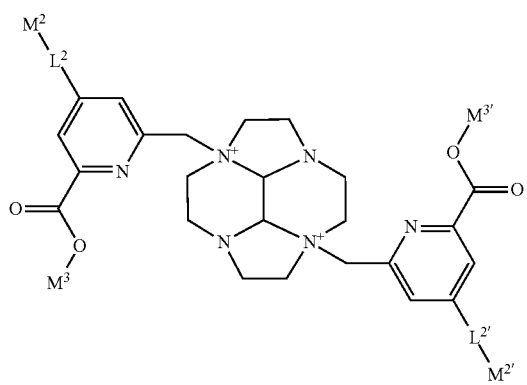

(vi')

wherein L², L²' are as defined in formula (I) and wherein M², M²', M³ and M³', are as defined above;

(c) deprotecting glyoxal bridge of compound (vi'), to afford compound (vii)

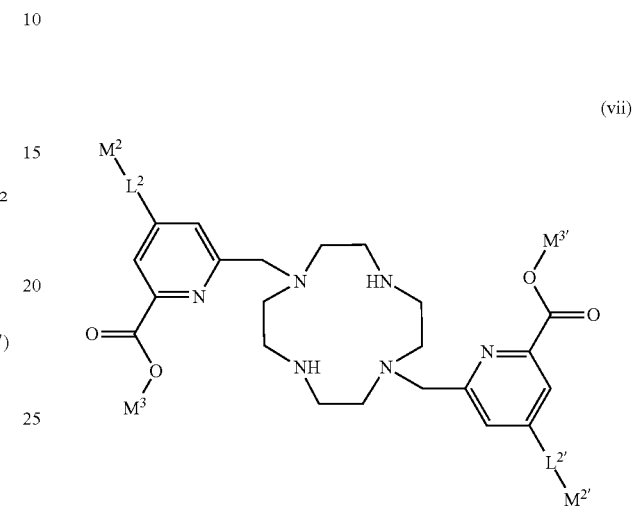

(vii)

wherein L², L²' are as defined in formula (I) and wherein M², M²', M³ and M³', are as defined above;

(a1) reacting (vii) with compound M¹-L¹-X¹ wherein
- L¹ is as defined in formula (I);
- X¹ represents a halogen atom, preferably Br or I;
- M¹ represents R¹, wherein R¹ is as defined in formula (I); or M represents a precursor of a coupling function;

to afford compound (viii)

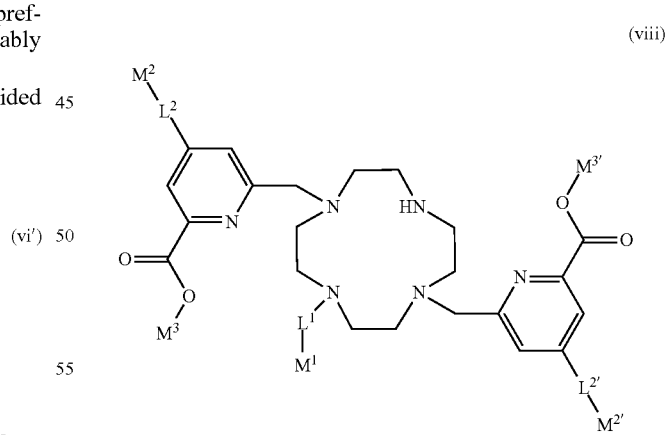

(viii)

wherein L¹, L², L²' are as defined in formula (I) and wherein M¹, M², M²', M³ and M³', are as defined above;

(a1') reacting (viii) with compound M¹'-L¹'-X¹' wherein
- L¹' is as defined in formula (I);
- X¹' represents a halogen atom, preferably Br or I;
- M¹' represents R¹', wherein R¹' is as defined in formula (I); or M¹' represents a precursor of a coupling function;

to afford compound (iii')

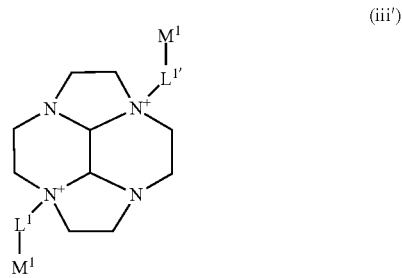

(iii')

wherein $L^1$, $L^{1'}$, $M^1$ and $M^{1'}$ are as defined above;
to afford intermediate compound (ii)

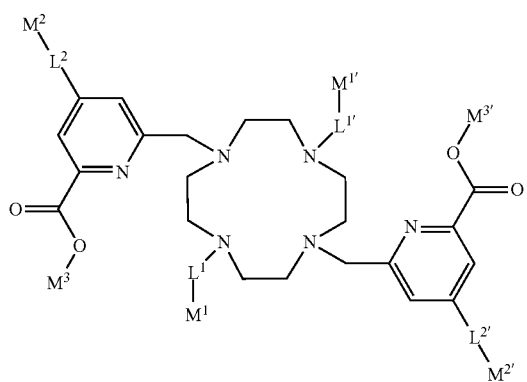

(ii)

wherein $L^1$, $L^{1'}$ $L^2$, $L^{2'}$ are as defined in formula (I) and wherein $M^1$, $M^{1'}$, $M^2$, $M^{2'}$, $M^3$ and $M^{3'}$, are as defined above;
and where needed, conducting on intermediate compound (ii) one or more subsequent step selected from:
  in the case wherein $M^1$, $M^{1'}$, $M^2$ or $M^{2'}$ represents a precursor of a coupling function, converting the precursor to a coupling function to afford compound of formula (I) wherein $R^1$, $R^{1'}$, $R^2$ or $R^{2'}$ respectively represents a coupling function;
  in the case wherein $M^1$, $M^{1'}$, $M^2$ or $M^{2'}$ represents a coupling function, introducing a bioactive group to afford compound of formula (I) wherein $R^1$, $R^{1'}$, $R^2$ or $R^{2'}$ respectively represents a bioactive group;
  in the case wherein $M^3$ or $M^{3'}$ represents a protecting group, deprotecting the acidic function, to afford compound of formula (I) wherein $R^3$ or $R^{3'}$ represent a hydrogen atom;
  introducing an activating function or a bioactive group on the acidic function to afford compound of formula (I) wherein $R^3$ or $R^{3'}$ represents an activating function or a bioactive group;
to afford compound of formula (I).

The present invention further relates to a process of manufacturing of the chelate of the invention.

According to one embodiment, the process for manufacturing a chelate according to the invention comprises reacting a ligand of formula (I) according to the invention with a metallic cation selected from bismuth (III), lead (II), copper (II), copper (I), gallium (III), zirconium (IV), technetium (III), indium (III), rhenium (VI), astatine (III), yttrium (III), samarium (III), actinium (III), lutetium (III), terbium (III), holmium (III), gadolinium (III), europium(III).

In a specific embodiment, the process for manufacturing a chelate according to the invention comprises reacting a ligand of formula (I) according to the invention with a metallic cation selected from bismuth (III), lead (II), preferably lead (II).

In an embodiment, the process of manufacturing the chelate of the invention comprises reacting the ligand of formula (I) of the invention with a metallic cation in an aqueous medium, preferably by adjusting the pH around neutrality with KOH. The process of the invention is preferably conducted at a temperature ranging from room temperature to reflux, preferably at room temperature. Chelation process is generally performed for a period ranging from few minutes to 24 hours, preferably a few minutes.

In an embodiment, the metallic cation used in the process the invention is under the form of a salt, preferably perchlorate, chloride, bromide, nitrates, sulfates, acetate, triflate salts.

Use of the Chelate

The invention is further directed to the use of the chelates of the invention in nuclear medicine, preferably as imaging agents and/or medicaments, preferably as radiopharmaceuticals.

The chelates of the invention are useful as medicaments. In particular, chelates of radioisotopes, preferably chelates of $^{212}$Bi ($^{212}$Pb), $^{213}$Bi, $^{225}$Ac, $^{67}$Cu, $^{188}$Re, $^{211}$At, $^{90}$Y, $^{153}$Sm, $^{177}$Lu or $^{149}$Tb may be used in RIT. Depending on the bioactive group present on the chelate, a broad variety of diseases may be targeted. For example, the following diseases may be targeted using specified bioactive groups:

| Diseases | Bioactive group name | type |
|---|---|---|
| lymphomes | anti-CD20 | antibody |
| prostate cancer | anti-CEA | antibody |
|  | bombesine | peptide |
|  | anti-PSMA | antibody/minibody |
|  | Lys-urea-Asp sequence | small molecule |
| breast cancer | anti-HER2 | antibody |
| colorectal cancer | anti-EGFR | antibody |
| neuroendocrine tumors | somatostatine analogues such as octreotide, TATE, TOC | peptide |

-continued

| | Bioactive group | |
|---|---|---|
| Diseases | name | type |
| tumoral neoangiogenesis | RGD analogues (for integrin targeting) | peptide |
| bones cancer | bisphosphonate derivatives | small molecule |
| medullar thyroid cancer | minigastrin | peptide |
| melanoma | α-MSH analogs | peptide |
| | benzamide derivatives | small molecule |
| glioblastoma | P substance | peptide |
| cancers (leukemia, breast, prostate, pancreas, lung, ovarian, colorectal . . .) | chemokine antagonists | peptides |

The chelates of the invention are also useful as imaging agents. In particular, chelates of radioisotopes, preferably chelates of $^{64}$Cu, $^{68}$Ga, $^{89}$Zr, $^{99m}$Tc, $^{111}$In, $^{186}$Re, or $^{166}$Ho may be used in PET imaging and/or in SPECT imaging. Chelates of gadolinium (III) may be used in MRI imaging. Chelates of lanthanides, preferably chelates of Eu(III), Tb(III) or Yb(III), may be used for imaging by luminescence.

The invention thus provides methods of treatment and/or prevention of diseases, comprising the administration of a therapeutically effective amount of a chelate of the invention, preferably a chelate of a radioisotope, to a patient in need thereof.

The invention further provides the use of a chelate of the invention, preferably a chelate of a radioisotope, for the manufacture of a medicament, preferably a radiopharmaceutical.

According to one embodiment, the chelates of the invention may be administered as part of a combination therapy. Thus, are included within the scope of the present invention embodiments comprising co-administration of a compound of the present invention as active ingredient and additional therapeutic agents and/or active ingredients.

The present invention further relates to a pharmaceutical composition comprising the chelate of the invention in association with at least one pharmaceutically acceptable excipient.

The present invention further relates to a medicament comprising the chelate of the invention.

Generally, for pharmaceutical use, the chelates of the invention may be formulated as a pharmaceutical preparation comprising at least one chelate of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular, intradermal or subcutaneous injection or intravenous infusion), for intralesional administration, for submucosal administration, for intra-articular administration, for intracavitary administration, for topical administration (including ocular), for artery embolization, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable for such formulations, such as salts (especially NaCl), glucose, lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as buffers, antioxidants, lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Use of the Ligand

According to an embodiment, the ligand of the invention is used for the synthesis of a chelate according to the present invention.

According to an embodiment, the ligand of the invention may be used as chelating agent to form chelates which may be used as imaging agents or medicaments in nuclear medicine.

According to an embodiment, the ligand of the invention may be used as scavenging agent.

According to an embodiment, the ligand of the invention is used for depollution of liquid medium by trapping of metallic cations.

According to a specific embodiment, the ligand of the invention may be used in epuration of effluents contaminated with metals. Especially, the ligand of the invention may be used to trap lead or radioactive elements. In a preferred embodiment, the ligand of the invention is used for ultrapurification of liquids. In the present invention, "ultrapurification" refers to the purification of a contaminated solution to a level of contaminant which is much less than 1 ppm (part per million), and generally in the range of ppb (part per billion), ppt (part per trillion), or lower i.e. an ultrapure solution.

According to another embodiment, the ligand of the invention may be used in cation detection, preferably in detection of traces of metallic cations.

EXAMPLES

The present invention will be better understood with reference to the following examples. These examples are intended to representative of specific embodiments of the invention, and are not intended as limiting the scope of the invention.

I. Materials and Methods

All commercial reagents were used as received from the suppliers unless otherwise indicated. The solvents were freshly distilled prior to use and according to literature procedures. Cyclen glyoxal (perhydro-2a,4a,6a,8a-tetraazacyclopenta[f,g]acenaphthylene) was synthesized according to Le Baccon et al., New. J. Chem., 2001, 25, 1168-1174. 6-(Chloromethyl)pyridine-2-carboxylic acid methyl ester was synthesized according to Mato-Iglesias et al., Inorg. Chem. 2008, 47, 7840-7851. Spectral data were in accordance with the literature.

Analytical $^1$H and $^{13}$C NMR spectra were recorded on a Bruker AMX3-300 MHz spectrometer operating at 300.17 and 75.48 MHz, for $^1$H and $^{13}$C, respectively. All experiments were performed at 25° C. The signals are indicated as follows: chemical shift (ppm), multiplicity (s, singlet; br. s, broad singlet; d, doublet; t, triplet; m, multiplet; quint, quintuplet), coupling constants J in hertz (Hz). The abbreviations Am, Ar, Cq, Pic and Ph stand for aminal, aromatic, quaternary carbon, picolinate and phenyl, respectively.

Chromatographic methods: All reactions were monitored by thin-layer chromatography, which was performed on aluminium sheets covered with silica gel 60 F254. Visualization was realized by UV-light irradiation (254 and 365 nm) and/or developed with Dragendorf stain.

High resolution mass spectra (HRMS-ESI) were performed in positive Electrospray Ionisation (ESI+) mode by the Mass Spectrometry service of the ICOA (Institut de Chimie Organique et Analytique), Orléans, France.

II. Synthesis of the Ligands

II.1. Synthesis of Ligand I-1

Scheme 1: Synthetic route of ligand I-1

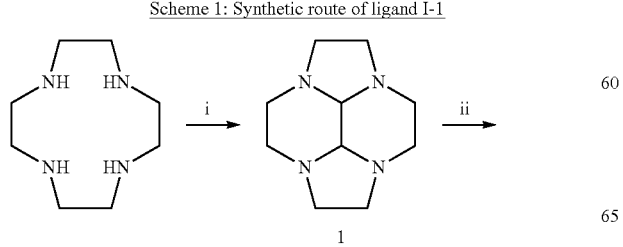

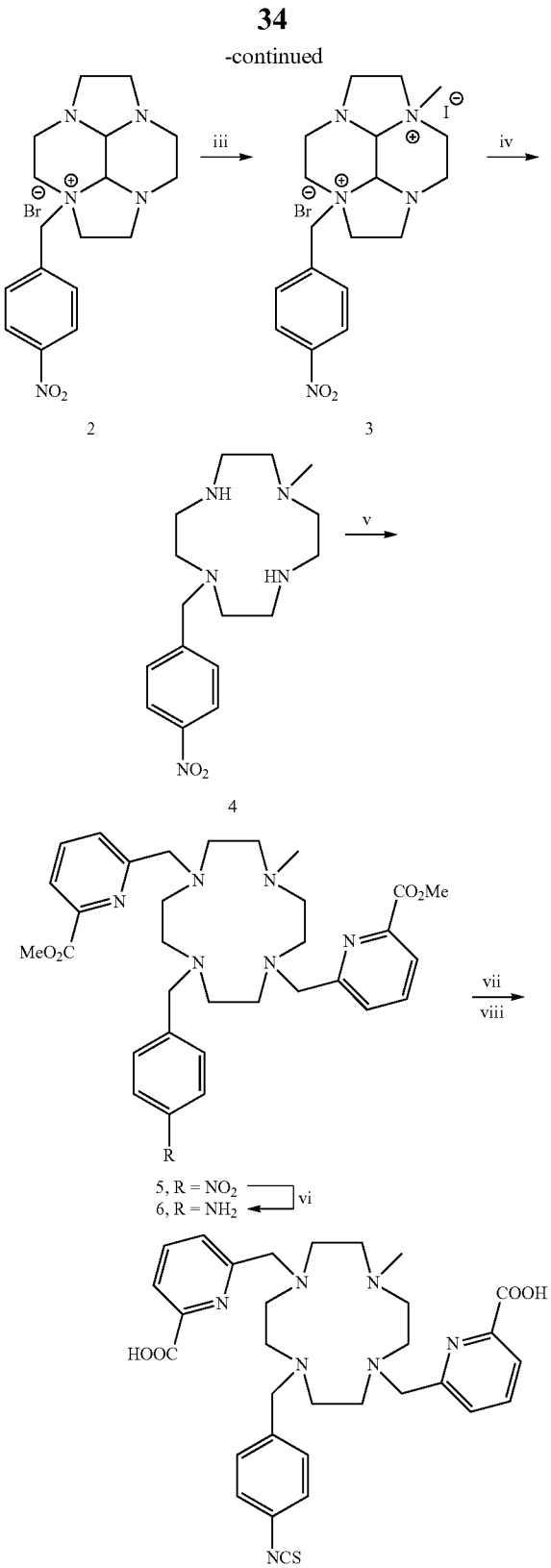

i) glyoxal, 40% aq., MeOH, r.t. 98%; ii) NO$_2$PhCH$_2$Br, THF, r.t., 96%; iii) CH$_3$I, CH$_3$CN, r.t., 95%; iv) 1,2-Diaminoethane, EtOH, r.t., 100%; v) methyl 6-(chloromethyl)picolinate, CH$_3$CN, r.t., 88%; vi) SnCl$_2$, HCl conc.:MeOH 1:1, r.t., 68% vii) HCl 6N, reflux; viii) CSCl$_2$, CH$_2$Cl$_2$, 24% (over two steps).

Intermediate 2

A solution of glyoxal cyclen 1 (5.14 g, 26.46 mmol) and 4-nitrobenzyl bromide (5.71 g, 26.46 mmol) in 30 mL of dry THF was stirred for 2 days at room temperature. The resulting white precipitate was collected by filtration and washed with dry THF to give a white solid (10.38 g, 96% yield).

$^1$H NMR (D$_2$O, 300 MHz): 8.34 (d, 2H, $^3$J=8.7), 7.85 (d, 2H, $^3$J=8.1), 5.06 (d, 1H, CH$_2$Ph, $^2$J=13.2), 4.85 (d, 1H, CH$_2$Ph, $^2$J=13.3), 4.26 (t, 1H, $^3$J=9.2), 4.12 (s, 1H, H$_{am}$), 3.82 (s, 1H, H$_{am}$), 3.72-3.52 (m, 4H), 3.33-3.17 (m, 5H), 2.97-2.77 (m, 4H), 2.57 (br. s, 2H). $^{13}$C NMR (D$_2$O, 300 MHz): 148.8 (CqNO$_2$), 133.6 (CqCH$_2$), 133.5 (2×CH$_{ar}$), 124.2 (2×CH$_{ar}$), 83.0 (CH$_{am}$), 71.4 (CH$_{am}$), 61.4 (CH$_2$Ph), 59.9, 57.0, 51.1, 48.0, 47.9, 47.3, 43.5. HRMS (ESI): calculated for C$_{17}$H$_{25}$N$_5$O$_2$$^+$ [M]: 330.192451; found: 330.192631.

Intermediate 3

Methyl iodide (1.05 mL, 16.93 mmol) was added to a stirred suspension of 2 (6.04 g, 14.72 mmol) in 25 mL of dry acetonitrile at room temperature. After stirring for 12 hours, the suspension was filtered and the filter cake washed with dry THF and then dried to obtain the desired compound pure (yellow solid, 7.73 g, 95%).

$^1$H NMR (D$_2$O, 300 MHz): 8.35 (d, 2H, 2×H$_{ar}$, $^3$J=7.5), 7.93 (d, 2H, 2×H$_{ar}$, $^3$J=7.7), 5.20 (d, 1H, CH$_2$Ph, $^3$J=13.2), 4.99 ((d, 1H, CH$_2$Ph, $^3$J=13.4), 4.86 (d, 2H, 2×H$_{am}$), 4.40 (t, 1H, $^3$J=8.8), 4.14-3.92 (m, 4H), 3.76-3.46 (m, 8H), 3.53 (s, 3H, CH$_3$) 3.33-3.24 (m, 3H). $^{13}$C NMR (D$_2$O, 300 MHz): 151.9 (CqNO$_2$), 136.7 (2×CH$_{ar}$), 136.0 (CqCH$_2$), 127.5 (2×CH$_{ar}$), 80.9 (CH$_{am}$), 80.8 (CH$_{am}$), 67.7 (CH$_2$Ph), 64.1, 62.4, 61.9, 57.8, 49.5, 49.2, 49.0, 45.8, 45.4. HRMS (ESI): calculated for C$_{18}$H$_{29}$N$_5$O$_2$ [M+2H]$^{2+}$: 172.607689; found: 172.608108.

Intermediate 4

To a suspension of 3 (7.73 g, 14.02 mmol) in 40 mL of EtOH, was added 1,2-ethylenediamine (2.81 mL, 42.07 mmol). The reaction mixture was stirred for 6 hours at room temperature. The solvent was then removed under reduced pressure and the resulting residue was partitioned between CH$_2$Cl$_2$ and water. The aqueous layer was further extracted twice with CH$_2$Cl$_2$, and the organic layers were combined and dried over anhydrous MgSO$_4$. The solvent was removed under vacuum to yield intermediate 4 as a pale yellow solid (5.07 g, 100%). No purification step was required.

$^1$H NMR (CDCl$_3$, 300 MHz): 8.07 (d, 2H, 2×H$_{ar}$, $^3$J=8.7), 7.46 (d, 2H, 2×H$_{ar}$, $^3$J=8.7), 5.93 (s, 2H, 2NH), 3.77 (s, 2H, CH$_2$Ph), 2.73-2.64 (m, 12H), 2.57-2.53 (m, 4H), 2.41 (s, 3H, CH$_3$). $^{13}$C NMR (CDCl$_3$, 300 MHz): 147.1 (Cq), 146.9 (Cq), 129.4 (2×CH$_{ar}$), 123.4 (2×CH$_{ar}$), 60.2 (CH$_2$Ph), 53.5, 52.2, 46.2, 44.2 (CH$_3$). HRMS (ESI): calculated for C$_{16}$H$_{28}$N$_5$O$_2$ [M+H]$^+$: 322.223752; found: 322.224088.

Intermediate 5

To a mixture of 4 (0.50 g, 1.55 mmol) and methyl 6-(chloromethyl)-2-pyridinecarboxylate (0.58 g, 3.11 mmol) in dry acetonitrile (10 mL) was added K$_2$CO$_3$ (0.90 g, 6.53 mmol). The solution was stirred under nitrogen at room temperature for 7 days. The undissolved materials were removed by filtration. Upon the evaporation of the solvent in vacuo, the crude product was dissolved in CH$_2$Cl$_2$ and the white precipitate was filtered off. The solvent was removed by evaporation under vacuum to afford the crude product (yellow oil, 0.74 g, 88%), which was taken onto the next step without further purification.

$^{13}$C NMR (CDCl$_3$, 300 MHz): 165.1 (2×CO), 159.0 (Cq$_{ar}$), 147.1 (Cq$_{ar}$), 146.3 (Cq$_{ar}$), 140.6 (CH$_{ar}$), 138.5 (CH$_{ar}$), 131.6 (CH$_{ar}$), 127.5 (CH$_{ar}$), 123.6 (CH$_{ar}$), 122.9 (CH$_{ar}$), 59.3 (2×CH$_2$Pic), 55.6 (CH$_2$PhNO$_2$), 53.4, 52.8 (2×CO$_2$CH$_3$), 50.5 (br), 44.0 (CH$_3$). HRMS (ESI): calculated for C$_{32}$H$_{42}$N$_7$O$_6$ [M+H]$^+$: 620.319109; found: 620.318734.

Intermediate 6

Tin(II) chloride (3.22 g, 14.28 mmol) was added to a stirred solution of the crude intermediate 5 (1.77 g, 2.86 mmol) in concentrated hydrochloric acid (40 mL) and MeOH (4 mL). The resulting solution was stirred at room temperature for 2 hours and the completion of reaction was monitored by mass spectrometry. The reaction mixture was neutralized at 0° C. by cautiously adding saturated aqueous Na$_2$CO$_3$. The product was then extracted with CH$_2$Cl$_2$ (3×50 mL). The organic layer was dried over anhydrous MgSO$_4$, filtered and evaporated under reduced pressure. The crude was purified by flash chromatography on alumina (CH$_2$Cl$_2$->CH$_2$Cl$_2$:MeOH 98:2) to give 6 as yellow oil (1.15 g, 68% yield).

$^1$H NMR (CDCl$_3$, 300 MHz): 7.88-7.79 (m, 4H, 4×H$_{ar}$), 7.55 (d, 2H, 2×H$_{ar}$, $^3$J=7.5), 6.52 (d, 2H, 2×H$_{ar}$, $^3$J=8.4), 6.40 (d, 2H, 2×H$_{ar}$, $^3$J=8.1), 3.84 (s, 2H), 3.73 (s, 2H), 3.35 (s, 6H, 2×CO$_2$CH$_3$), 3.15 (s, 2H, CH$_2$PhNH$_2$), 3.01-2.09 (m, 16H), 1.73 (s, 3H, CH$_3$). $^{13}$C NMR (CDCl$_3$, 300 MHz): 164.6 (CO), 158.5 (Cq), 145.9 (Cq), 145.6 (Cq), 138.1 (CH$_{ar}$), 130.9 (CH$_{ar}$), 127.0 (CH$_{ar}$), 123.1 (CH$_{ar}$), 121.5 (Cq), 113.9 (CH$_{ar}$), 58.7, 55.4, 52.1 (2×CO$_2$CH$_3$), 43.6 (CH$_3$). HRMS (ESI): calculated for C$_{32}$H$_{44}$N$_7$O$_4$ [M+H]$^+$: 590.344929; found: 590.344450.

Ligand I-1

Intermediate 6 (1.30 g, 2.20 mmol) was dissolved in 5 mL of hydrochloric acid (6 M), and refluxed 48 h to hydrolyse the methyl esters. The reaction mixture was allowed to cool down to ambient temperature, and after being diluted by water (5 mL) and CH$_2$Cl$_2$ (5 mL), thiophosgene (2.53 mL, 33.06 mmol) was added carefully. The mixture was kept under vigorous stirring for 12 hours, followed by decanting of the organic phase with a pipet to remove excess thiophosgene. The aqueous layer was washed with CH$_2$Cl$_2$ (3×5 mL) by vigorous biphasic stirring. The aqueous layer was loaded directly onto a RP-HPLC. The solvent system used had the following time profile with a run time of 25 min: 0-3 min: 90% solvent A (0.1% HCOOH in water) and 10% of solvent B (0.1% HCOOH in MeCN); 3-25 min: 90% of solvent A declining to 45% with the solvent B rising to 55% over the same time interval. Flow rate: 5 mL/min. Detector: 254 nm. Retention time: 15 min. Removal of solvents by lyophilization gave the desired ligand as pale yellow powder.

$^{13}$C NMR (D$_2$O, 300 MHz): 168.3 (CO), 158.3 (Cq$_{ar}$-CH$_2$), 148.0 (Cq$_{ar}$-CO$_2$H), 144.2 (CH$_{ar}$), 139.3 (CN), 135.8, 135.1, 131.9, 131.2, 129.7, 128.6, 128.3, 128.2, 126.6, 65.1 (2×CH$_2$Pic), 64.7 (CH$_2$PhNCS), 58.9, 57.8, 55.7, 52.7, 50.4, 46.3 (CH$_3$). HRMS (ESI): calculated for C$_{31}$H$_{38}$N$_7$O$_4$S [M+H]$^+$: 604.270050; found: 604.269622.

II.2. Synthesis of Ligand I-2

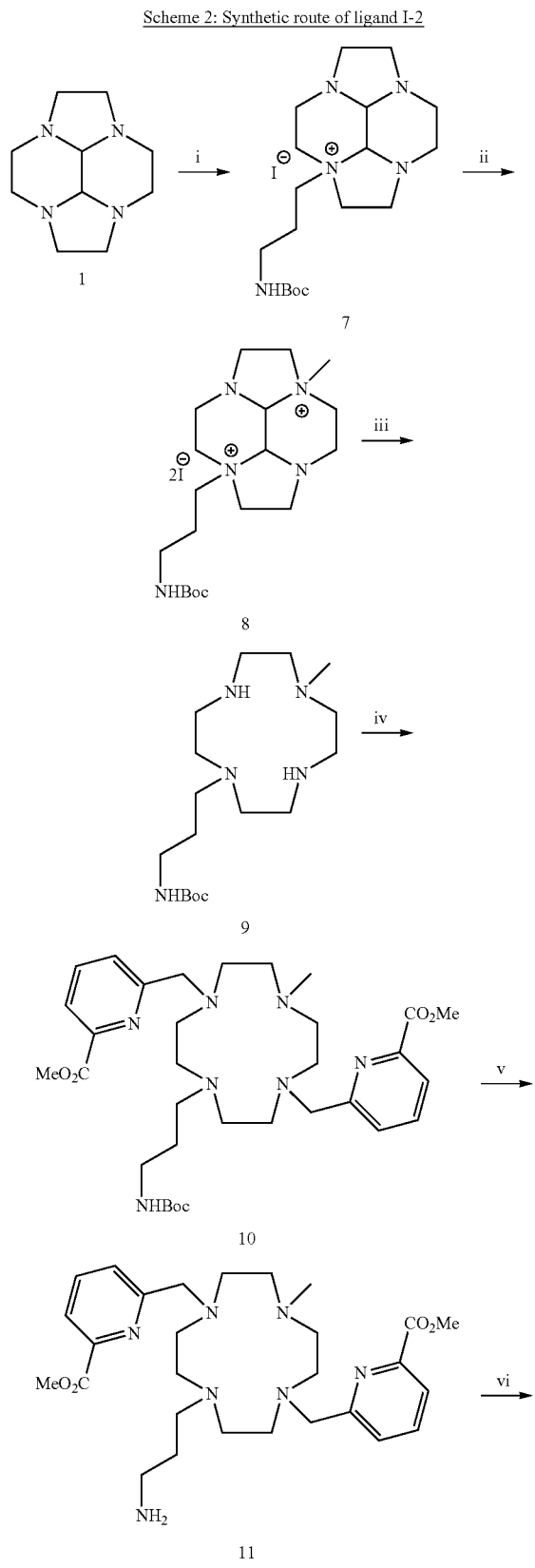

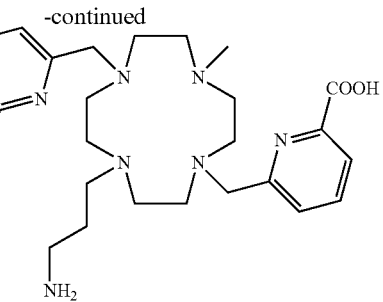

I-2 i) BocNH(CH$_2$)$_3$I, THF, r.t., 91%; ii) CH$_3$I, CH$_3$CN, r.t., 92%; iii) NH$_2$CH$_2$CH$_2$NH$_2$, CH$_2$Cl$_2$, r.t., 100%; iv) methyl 6-(chloromethyl)picolinate, CH$_3$CN, r.t., 88%; v) H$_3$PO$_4$ 85% aq., CH$_2$Cl$_2$, r.t. 91%; vi) HCl 6N, reflux.

Intermediate 7.

A solution of glyoxal cyclen 1 (1.00 g, 5.15 mmol) and tert-butyl N-(3-iodopropyl)carbamate (1.64 g, 5.66 mmol) in 10 mL of dry THF was stirred for 4 days at room temperature. The resulting precipitate was recovered by filtration and washed with small portions of dry THF, to give a white solid (2.25 g, 91% yield).

$^1$H NMR (D$_2$O, 300 MHz): 3.95-3.41 (m, 10H), 3.27-3.17 (m, 6H), 2.95-2.76 (m, 4H), 2.58-2.47 (m, 2H), 2.14-2.00 (m, 2H, CH$_2$CHNHBoc), 1.44 (s, 9H, C(CH$_3$)$_3$). $^{13}$C NMR (D$_2$O, 300 MHz): 161.3 (CO), 87.1 (CH$_{am}$), 84.6 (C(CH$_3$)$_3$), 75.0 (CH$_{am}$), 65.3, 60.3, 9.3 (CH$_2$NHCO), 54.5, 51.7, 51.4, 51.0, 50.9, 46.9, 40.3 (CH$_2$NHCO), 31.1, 26.7 (CH$_2$CH$_2$NHCO). HRMS (ESI): calculated for C$_{18}$H$_{34}$N$_5$O$_2$ [M+H]$^+$: 352.270702; found: 352.270888.

Intermediate 8.

A solution of 7 (0.62 g, 1.29 mmol) and iodomethane (0.085 mL, 1.36 mmol) in 10 mL of dry acetonitrile was allowed to stir overnight at room temperature. The resulting precipitate was recovered by filtration and washed with small portions of dry acetonitrile, to yield a white powder (0.74 g, 92%).

$^1$H NMR (D$_2$O, 300 MHz): 4.57 (s, 2H, 2×H$_{am}$), 4.10-3.39 (overlapping m, 14H), 3.43 (s, 3H, CH$_3$), 3.27-3.10 (m, 6H), 2.22-1.99 (m, 2H, CH$_2$CHNHBoc), 1.46 (s, 9H, C(CH$_3$)$_3$). $^{13}$C NMR (D$_2$O, 300 MHz): 161.0 (CO), 84.2 (C(CH$_3$)$_3$), 81.4 (CH$_{am}$), 80.9 (CH$_{am}$), 67.8, 64.5, 62.0, 58.6, 57.9, 49.6 (CH$_3$), 49.2, 45.8, 45.4, 39.8 (CH$_2$NH), 30.7 (C(CH$_3$)$_3$), 26.2 (CH$_2$CH$_2$NHCO). HRMS (ESI): calculated for C$_{19}$H$_{37}$N$_5$O$_2$$^{2+}$ [M+2H]$^{2+}$: 183.646814; found: 183.647112.

Intermediate 9.

To a suspension of 8 (0.58 g, 0.93 mmol) in 15 ml of CH$_2$Cl$_2$, was slowly added 1,2-ethanediamine (0.25 mL, 3.73 mmol) at room temperature. The reaction mixture was stirred overnight. 1,4,5,8-Tetrazaperhydronaphthalene (tetrazadecaline) appeared as a white precipitate which was removed by filtration. The filtrate was concentrated in vacuo to provide the pure compound without recourse to chromatography (white solid, 0.32 g, quantitative yield).

$^1$H NMR (CDCl$_3$, 300 MHz): 3.12 (m, 4H, CH$_2$NH & 2H), 2.65-2.43 (m, 18H, 9CH$_2$), 2.28 (s, 3H, CH$_3$), 1.64 (quint, 2H, CH$_2$CH$_2$NHBoc), 1.40 (s, 9H, C(CH$_3$)$_3$). $^{13}$C NMR (CDCl$_3$, 300 MHz): 156.3 (CO), 78.7 (Cq), 54.0, 53.3 (CH$_2$(CH$_2$)$_2$NHBoc), 51.4, 46.3, 46.1, 44.0, 44.0 (CH$_3$), 37.5 (CH$_2$NHBoc), 28.2 (C(CH$_3$)$_3$), 27.8 (CH$_2$CH$_2$NHBoc). HRMS (ESI): calculated for C$_{17}$H$_{38}$N$_5$O$_2$ [M+H]$^+$: 344.302002; found: 344.302210.

Intermediate 10.

To a solution of 9 (0.45 g, 1.31 mmol) and methyl 6-(chloromethyl)-2-pyridinecarboxylate (0.51 g, 2.76 mmol) in dry acetonitrile was added $K_2CO_3$ (0.91 g, 6.58 mmol). The solution was stirred at room temperature for 5 days. The undissolved materials were filtered off and the solvent was removed under reduced pressure. The residue was taken up with $CH_2Cl_2$. After removal of the white precipitate by filtration, the product was simply obtained by evaporating the solvent (yellow oil, 0.74 g, 88%). The crude product was used for next step without further purification.

$^1$H NMR (CDCl$_3$, 300 MHz): 8.04-7.91 (m, 4H, 4H$_{ar}$), 7.58 (d, 1H, H$_{ar}$, $^3$J=7.5), 3.87 (s, 6H, 2×CO$_2$CH$_3$), 3.13-2.16 (m, 20H), 1.98 (s, 3H, CH$_3$), 1.55-1.47 (m, 2H, CH$_2$CH$_2$NHBoc), 1.34 (s, 9H, C(CH$_3$)$_3$). $^{13}$C NMR (CDCl$_3$, 300 MHz): 164.9 (CO), 158.9, 146.6, 138.2, 127.4, 123.5, 78.2 (C(CH$_3$)$_3$), 60.6 (2×CH$_2$Pic), 52.4 (2CO$_2$CH$_3$), 50.6, 50.4, 42.8 (NCH$_3$), 38.3 (CH$_2$NH$_2$), 27.2 (C(CH$_3$)$_3$), 23.5 (CH$_2$CH$_2$NHBoc). HRMS (ESI): calculated for C$_{33}$H$_{52}$N$_7$O$_6$ [M+H]$^+$: 642.397359; found: 642.396805.

Intermediate 11.

To a solution of 10 (0.23 g, 0.36 mmol) in $CH_2Cl_2$ (5 mL) at room temperature was added dropwise aqueous phosphoric acid (85 wt %) (0.15 mL, 2.15 mmol). The mixture was vigorously stirred for 3 h, and TLC showed reaction completion. The supernatant was removed and the solid gum was washed with $CH_2Cl_2$ (2×5 mL). 5 mL of MeOH was then added to dissolve the solid residue and an aqueous 6N NaOH solution was added slowly to adjust the pH to 7. The precipitated salt was removed and the mixture was concentrated in vacuo. The resulting residue was taken up with $CH_2Cl_2$ and the white precipitate removed by filtration. The filtrate was dried under reduced pressure to give the desired product as a light yellow foam (0.64 g, 91%). No purification was deemed necessary.

$^1$H NMR (CDCl$_3$, 300 MHz): 8.05 (d, 2H, 2×H$_{ar}$, $^3$J=6.0 Hz), 7.94 (t, 2H, 2×H$_{ar}$, $^3$J=6.0), 7.61 (d, 2H, 2×H$_{ar}$, $^3$J=5.7), 4.13 (m, 2H, CH$_2$Pic), 3.98 (s, 6H, 2×CO$_2$CH$_3$), 3.66 (m, 2H, CH$_2$Pic), 2.91-2.40 (overlapping m, 20H), 2.02-1.88 (m, 2H, CH$_2$CH$_2$NH$_2$), 1.67 (s, 3H, CH$_3$). $^{13}$C NMR (CDCl$_3$, 300 MHz): 164.7 (CO), 158.0 (C$_{ar}$), 146.7, 138.0 (C$_{ar}$), 127.7 (C$_{ar}$), 123.6 (C$_{ar}$), 61.7 (2×CH$_2$Pic), 53.5, 52.4 (2×CO$_2$CH$_3$), 51.7, 51.5, 50.5, 50.3, 42.1 (CH$_3$), 39.4 (CH$_2$NH$_2$), 23.6 (CH$_2$CH$_2$NH$_2$). HRMS (ESI): calculated for C$_{28}$H$_{44}$N$_7$O$_4$ [M+H]$^+$: 542.344929; found: 542.344902.

Ligand I-2.

Intermediate 11 was dissolved in hydrochloric acid (6 M), and refluxed 48 h to hydrolyze the methyl esters. The reaction mixture was allowed to cool down to ambient temperature. Removal of solvents under reduce pressure gave the desired ligand under its chlorhydrate form.

II.3. Conjugation of I-1 to di-HSGL Affording I-3

Ligand I-1 (Me-do2pa-PhNCS) was coupled to di-HSGL hapten, a synthetic peptide of low molecular weight, leading to ligand I-3, as presented in the scheme below:

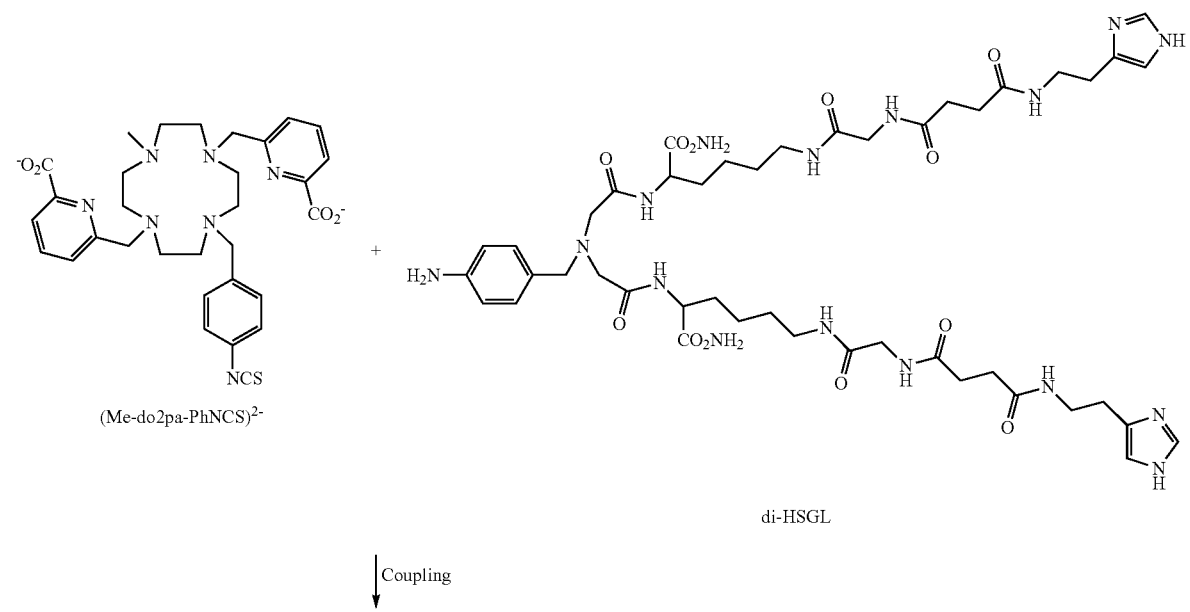

-continued

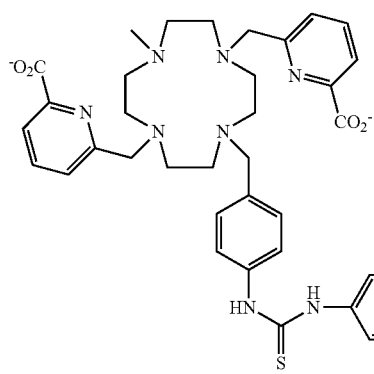

3.5 equivalents of (Me-do2pa-PhNCS)²⁻ and 1 equivalent of di-HSGL were dissolved in a 0.2 M MES buffer solution (2-morpholino ethanesulfonic acid monohydrate) at pH 6.1. The solution was incubated at room temperature and stirred for 16 h.

The coupling was analyzed by HPLC, with a Cis symmetry shield column (isocratic mode 15% ACN/85% TFA (0.5% in water), UV detection λ=254 nm, 1 mL/min). A main peak at rt=14.5 min that corresponds to the coupling product between (Me-do2pa-PhNCS)²⁻ and di-HSFL was detected.

The coupling product between (Me-do2pa-PhNCS)²⁻ and di-HSGL (i.e. ligand I-3) was purified by HPLC, in the same conditions as described above.

III. Synthesis of the Chelates

Formation of the Lead Chelates.

The ligand is dissolved in $H_2O$ and $PbCl_2$ (1 eq) is added to the solution followed if necessary by a few drops of concentrated HCl until complete dissolution of $PbCl_2$. The solution is stirred at room temperature for 30 min. The pH is raised to pH=7 by addition of KOH. The resulting mixture is stirred for a few hours under reflux. The reaction mixture is cooled down to room temperature and MeOH is added. The precipitate is filtered off. The filtrate is evaporated and washed several times with MeOH to yield to lead chelate.

Formation of the Bismuth Chelates.

The ligand is dissolved in 3 mL of $H_2O$ and concentrated HCl in order to have a starting pH around 1. Then, 1 eq. of $Bi(NO_3)_3 \cdot 5H_2O$ is added. The mixture is stirred at room temperature for 30 min. The pH is raised to pH=4 by addition of KOH. A white precipitate appears. The resulting mixture is stirred for a few hours under reflux. The reaction mixture is cooled down to room temperature and MeOH is added. The precipitate is filtered off. The filtrate is evaporated and washed several times with MeOH to give the bismuth chelate.

Radiolabeling of Di-HSGL Ligand I-3 with 213Bi.

Bismuth-213 was eluted in 600 μL of water. A solution comprising 5 μL of ligand I-3 (0.195 nmol), 60 μL tris pH7 (2M), 20 μL NaOH (2.5 M) and 500 μL of elute (440 μCi) was prepared and incubated 15 min at 92° C.

Radiolabeling was analyzed by ITLC-SG, with a 0.1M citrate buffer pH5. The radiolabeling yield was of 50% leading to a specific activity of 42 MBq/nmol.

The resulting $^{213}$Bi radiolabeled chelate was purified on Sep-Pak Oasis (Waters).

The invention claimed is:

1. A chelate resulting from the complexation of a ligand of formula (Ia)

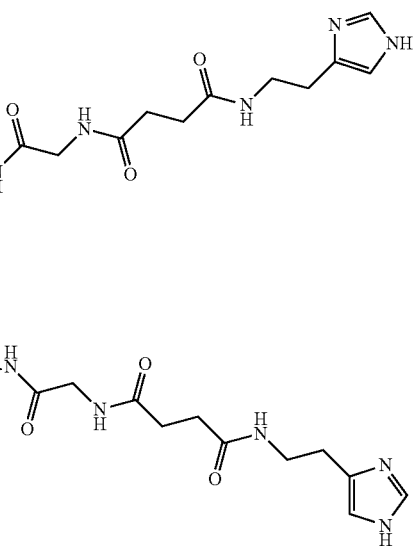

(Ia)

or a basic salt thereof;
wherein
$R^1$ and $R^{1'}$ each independently represents:
   a hydrogen atom;
   a coupling function, wherein the coupling function is selected from the group consisting of amine; isothiocyanate; isocyanate;
N-hydroxysuccinimide ester, N-hydroxyglutarimide ester, maleimide ester; carboxylic acid; acid anhydride, acid halide; alcohol; alkyne; halide; azide; siloxy; phosphonic acid; thiol; tetrazine; norbornen; oxoamine; aminooxy; thioether; haloacetamide; glutamate; glutaric anhydride, succinic anhydride, maleic anhydride; aldehyde; ketone; hydrazide; chloroformate; and maleimide; or
   a bioactive group, wherein the bioactive group is a peptide;
$L^1$ and $L^{1'}$ each independently represents:
   a single bond; or
   a linker selected from the group consisting of alkyl, aryl, arylalkyl, alkylaryl, heteroaryl, heteroarylalkyl, alkylheteroaryl, alkenyl, and alkynyl; wherein alkyl moieties are optionally interrupted by one or more heteroatoms selected from the group consisting of O, N, and S; optionally additionally comprising a residue of a coupling function through which $R^1$ and $R^{1'}$ are bounded to $L^1$, and $L^{1'}$ respectively;

provided that at least one of $-L^1-R^1$ and $-L^{1'}-R^{1'}$ represents a linker with a coupling function or a linker with a bioactive group;

with a metallic cation selected from the group consisting of bismuth (III), lead (II), copper (II), copper (I), gallium (III), zirconium (IV), technetium (III), indium (III), rhenium (VI), astatine (III), yttrium (III), samarium (III), actinium (III), lutetium (III), terbium (III), holmium (III), gadolinium (III), europium (III), and $^{212}Bi(^{212}Pb)$.

2. The chelate according to claim 1, wherein at least one of $-L^1-R^1$ and $-L^{1'}-R^{1'}$ is selected from formulae (a) and (b):

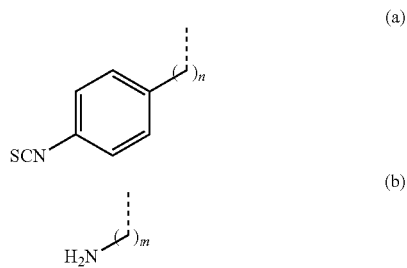

(a)

(b)

wherein n and m represent each independently an integer ranging from 1 to 10.

3. The chelate according to claim 2, wherein n and m represent each independently 1, 2, 3, or 4.

4. The chelate according to claim 1, wherein $L^{1'}$ is an alkyl linker and $R^{1'}$ is a hydrogen atom.

5. The chelate according to claim 1, wherein the peptide is di-HSGL.

6. The chelate according to claim 1, wherein the ligand is selected from the group consisting of 6,6'-((4-(4-isothiocyanatobenzyl)-10-methyl-1,4,7, 10-tetraazacyclododecane-1, 7-diyl)bis(methylene)) dipicolinic acid;

6,6'-((4-(3-aminopropyl)-10-methyl-1,4,7, 10-tetraazacyclododecane -1, 7-diyl)bis(methylene)) dipicolinic acid;

6,6'-((4-(4-(3-(4-(6-((aminooxy)carbonyl)-2-(16-((aminooxy) carbonyl)-1-(1H-imidazol-4-yl)-4, 7, 10, 18-tetraoxo-3,8, 11, 17-tetraazanonadecan-19-yl)-21-(1H-imidazol-4-yl)-4, 12, 15, 18-tetraoxo-2,5, 11, 14, 19-pentaazahenicosyl)phenyl)thioureido)benzyl)-10-methyl-1,4, 7, 10-tetraazacyclododecane-1, 7-diyl) bis (methylene)) dipicolinate; and basic salts thereof.

7. The chelate according to claim 6, wherein the ligand is 6,6'-((4-(4-isothiocyanatobenzyl)-10-methyl-1,4, 7, 10-tetraazacyclododecane-1,7-diyl)bis(methylene)) dipicolinic acid or a basic salt thereof.

8. The chelate according to claim 6, wherein the ligand is 6,6'- ((4-(3-aminopropyl)-10-methyl-1,4, 7, 10-tetraazacyclododecane-1, 7-diyl)bis(methylene)) dipicolinic acid or a basic salt thereof.

9. The chelate according to claim 6, wherein the ligand is 6,6'-((4-(4-(3-(4-(6-((aminooxy)carbonyl)-2-(16-((aminooxy)carbonyl)-1-(1H -imidazol-4-yl) -4, 7, 10, 18-tetraoxo-3,8, 11, 17-tetraazanonadecan-19-yl)-21-(1H -imidazol-4-yl) -4, 12, 15, 18-tetraoxo-2,5, 11, 14, 19-pentaazahenicosyl)phenyl)thioureido)benzyl)-10-methyl-1,4,7,10-tetraazacyclododecane-1, 7-diyl)bis(methylene)) dipicolinate or a basic salt thereof.

10. The chelate according to claim 1, wherein the metallic cation is a radioisotope.

11. The chelate according to claim 1, wherein the metallic cation is a radioisotope selected from the group consisting of $^{212}Bi(^{212}Pb)$, $^{213}Bi(III)$, $^{64}Cu(II)$, $^{67}Cu(II)$, $^{68}Ga(III)$, $^{89}Zr$ (IV), $^{99m}Tc(III)$, $^{111}In(III)$, $^{186}Re(VI)$, $^{188}Re(VI)$, $^{211}At(III)$, $^{225}Ac(III)$, $^{90}Y(III)$, $^{177}Lu(III)$, $^{153}Sm(III)$, $^{149}Tb(III)$, and $^{166}Ho(III)$.

12. The chelate according to claim 1, wherein the metallic cation is a radioisotope selected from the group consisting of $^{212}Bi(^{212}Pb)$ and $^{213}Bi(III)$.

13. A process for manufacturing a chelate according to claim 1 comprising reacting a ligand of formula (Ia)

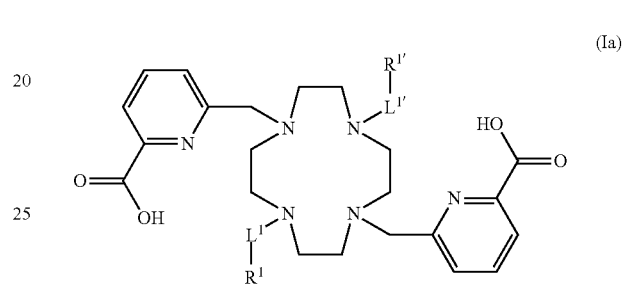

(Ia)

or a basic salt thereof;

wherein $R^1$ and $R^{1'}$ each independently represents:
  a hydrogen atom;
  a coupling function, wherein the coupling function is selected from the group consisting of amine; isothiocyanate; isocyanate; N-hydroxysuccinimide ester, N-hydroxyglutarimide ester, maleimide ester; carboxylic acid; acid anhydride, acid halide; alcohol; alkyne; halide; azide; siloxy; phosphonic acid; thiol;
  tetrazine; norbornen; oxoamine; aminooxy; thioether; haloacetamide; glutamate; glutaric anhydride, succinic anhydride, maleic anhydride; aldehyde; ketone; hydrazide; chloroformate; and maleimide; or
  a bioactive group, wherein the bioactive group is a peptide;

$L^1$ and $L^{1'}$ each independently represents:
  a single bond; or
  a linker selected from the group consisting of alkyl, aryl, arylalkyl, alkylaryl, heteroaryl, heteroarylalkyl, alkylheteroaryl, alkenyl, and alkynyl; wherein alkyl moieties are optionally interrupted by one or more heteroatoms selected from the group consisting of O, N, and S; optionally additionally comprising a residue of a coupling function through which $R^1$ and $R^{1'}$ are bounded to $L^1$, and $L^{1'}$ respectively;

provided that at least one of $-L^1-R^1$ and $-L^{1'}-R^{1'}$ represents a linker with a coupling function or a linker with a bioactive group;

with a metallic cation selected from the group consisting of bismuth (III), lead (II), copper (II), copper (I), gallium (III), zirconium (IV), technetium (III), indium (III), rhenium (VI), astatine (III), yttrium (III), samarium (III), actinium (III), lutetium (III), terbium (III), holmium (III), gadolinium (III), europium (III), and $^{212}Bi(^{212}Pb)$.

14. The process according to claim 13, wherein the metallic cation is a radioisotope selected from the group consisting of $^{212}$Bi($^{212}$Pb), $^{213}$Bi(III), $^{64}$Cu(II), $^{67}$Cu(II), $^{68}$Ga(III), $^{89}$Zr(IV), $^{99}$mTc(III), $^{111}$In(III), $^{186}$Re(VI), $^{188}$Re(VI), $^{211}$At(III), $^{225}$Ac(III), $^{90}$Y(III), $^{177}$Lu(III), $^{153}$Sm(III), $^{149}$Tb(III), and $^{166}$Ho(III).

15. The process according to claim 13, wherein the metallic cation is a radioisotope selected from the group consisting of $^{212}$Bi($^{212}$Pb) and $^{218}$Bi(III).

* * * * *